US010898681B2

(12) United States Patent
Khanicheh et al.

(10) Patent No.: US 10,898,681 B2
(45) Date of Patent: *Jan. 26, 2021

(54) ENDOSCOPIC CANNULATING DEVICES AND METHODS OF USE

(71) Applicant: HOYA Corporation, Tokyo (JP)

(72) Inventors: Azadeh Khanicheh, Somerville, MA (US); Isaac Ostrovsky, Wellesley, MA (US); Almir Velagic, Watertown, MA (US); Michael Barenboym, Boston, MA (US)

(73) Assignee: Hoya Corporation, Tokyo (JP)

( * ) Notice: Subject to any disclaimer, the term of this patent is extended or adjusted under 35 U.S.C. 154(b) by 585 days.

This patent is subject to a terminal disclaimer.

(21) Appl. No.: 15/653,731

(22) Filed: Jul. 19, 2017

(65) Prior Publication Data

US 2019/0022354 A1  Jan. 24, 2019

(51) Int. Cl.
*A61M 25/00* (2006.01)
*A61M 25/01* (2006.01)
(Continued)

(52) U.S. Cl.
CPC ..... *A61M 25/0097* (2013.01); *A61B 1/00112* (2013.01); *A61M 25/0015* (2013.01);
(Continued)

(58) Field of Classification Search
CPC .......... A61M 25/0015; A61M 25/0138; A61M 2025/0024; A61M 2025/018;
(Continued)

(56) References Cited

U.S. PATENT DOCUMENTS 4,988,356 A * 1/1991 Crittenden ........ A61M 25/0169
600/434
5,380,290 A * 1/1995 Makower ............. A61M 25/06
604/160

(Continued)

FOREIGN PATENT DOCUMENTS

WO    WO 1998/10821 A1    3/1998

OTHER PUBLICATIONS

Boston Scientific Corporation, May 2016, "Dreamtome™ RX Sphincterotome" ENDO-377607-AA (6 pages).

(Continued)

*Primary Examiner* — Nathan R Price
*Assistant Examiner* — Melissa A Snyder
(74) *Attorney, Agent, or Firm* — Finnegan, Henderson, Farabow, Garrett & Dunner, LLP

(57) ABSTRACT

Embodiments of the present disclosure are directed to cannulating devices and methods for exchanging cannulating devices in an endoscopic procedure. In one implementation, an apparatus for endoscopic operations is described. The apparatus includes a cannulating device to be introduced through an internal lumen of an endoscope via a biopsy port. The cannulating device has an elongated body. The elongated body includes a guidewire lumen configured to receive a guidewire therein, and a slit extending over at least a portion of the length of the elongated body from a distal tip to a proximal position of the elongated body.

15 Claims, 19 Drawing Sheets

(51) Int. Cl.
  *A61B 1/00* (2006.01)
  *A61M 25/10* (2013.01)
  *A61M 25/09* (2006.01)
(52) U.S. Cl.
  CPC .... *A61M 25/0138* (2013.01); *A61M 25/0169* (2013.01); *A61M 25/10* (2013.01); *A61M 2025/0042* (2013.01); *A61M 2025/09125* (2013.01); *A61M 2025/1004* (2013.01)
(58) Field of Classification Search
  CPC .... A61M 2025/1056; A61M 25/09041; A61M 2025/0136; A61M 25/0172; A61M 2025/0177; A61M 25/0136; A61M 25/0169; A61B 1/00085; A61B 1/0014; A61B 1/00121
  See application file for complete search history.

(56) References Cited

U.S. PATENT DOCUMENTS

| | | | |
|---|---|---|---|
| 6,159,198 A * | 12/2000 | Gardeski | A61M 25/0668 604/161 |
| 6,893,393 B2 | 5/2005 | Carrillo | |
| 7,172,577 B2 | 2/2007 | Mangano et al. | |
| 7,645,283 B2 | 1/2010 | Reynolds et al. | |
| 7,811,250 B1 * | 10/2010 | Scopton | A61M 29/02 604/103.04 |
| 2002/0143251 A1 | 10/2002 | Richardson et al. | |
| 2003/0233043 A1 | 12/2003 | Windheuser et al. | |
| 2004/0133185 A1 * | 7/2004 | Nash | A61M 25/0169 604/533 |
| 2005/0059990 A1 * | 3/2005 | Ayala | A61B 1/018 606/192 |
| 2014/0223701 A1 * | 8/2014 | Bean | A61B 1/00133 24/483 |

OTHER PUBLICATIONS

Boston Scientific Corporation, May 2016, "Trapezoid™ RX" ENDO-333814-AA (4 pages).
Boston Scientific Corporation, Jun. 2016, "Extractor™ Pro RX-S" ENDO-396406-AA (2 pages).
U.S. Appl. No. 15/585,487; System and Methods for Device Exchange in an Endoscopic Procedure; Azadeh Khanicheh et al; filed May 3, 2017.
U.S. Appl. No. 15/653,717; Endoscopic Balloon Catheter; Azadeh Khanicheh et al; filed Jul. 19, 2017.
U.S. Appl. No. 15/653,727; Endoscopic Basket Delivery Catheter; Azadeh Khanicheh et al; filed Jul. 19, 2017.
U.S. Appl. No. 15/653,737; Universal Retrieval Device for Removing Obstructions From Body Lumens; Azadeh Khanicheh et al; filed Jul. 19, 2017.
International Search Report and Written Opinion dated Oct. 23, 2018, for International Application No. PCT/IB2018/055362, filed Jul. 18, 2018.

* cited by examiner

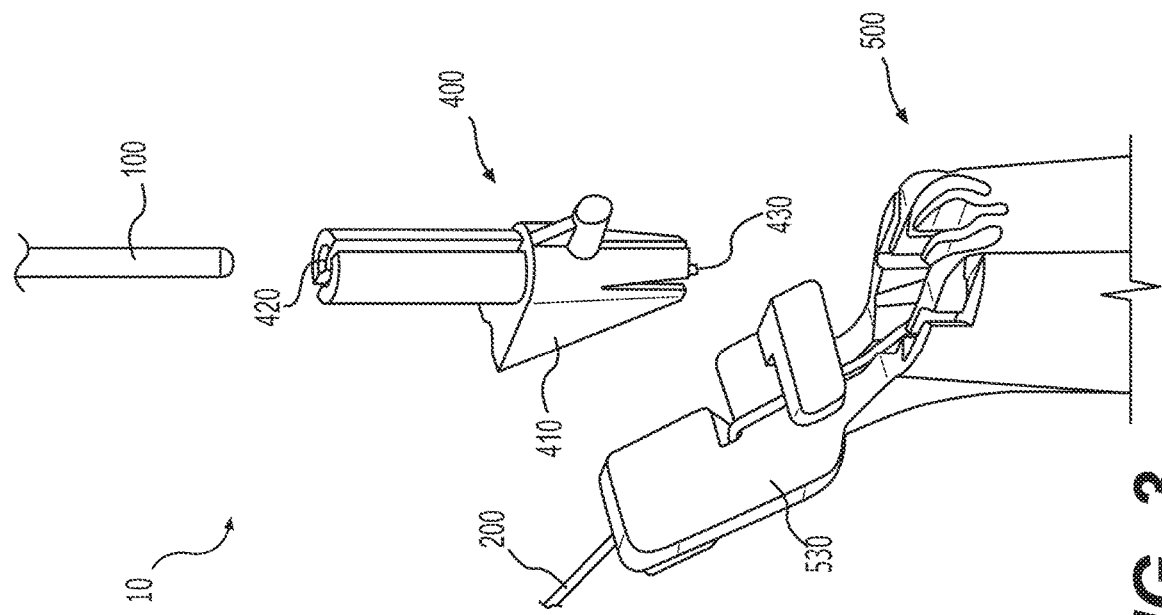
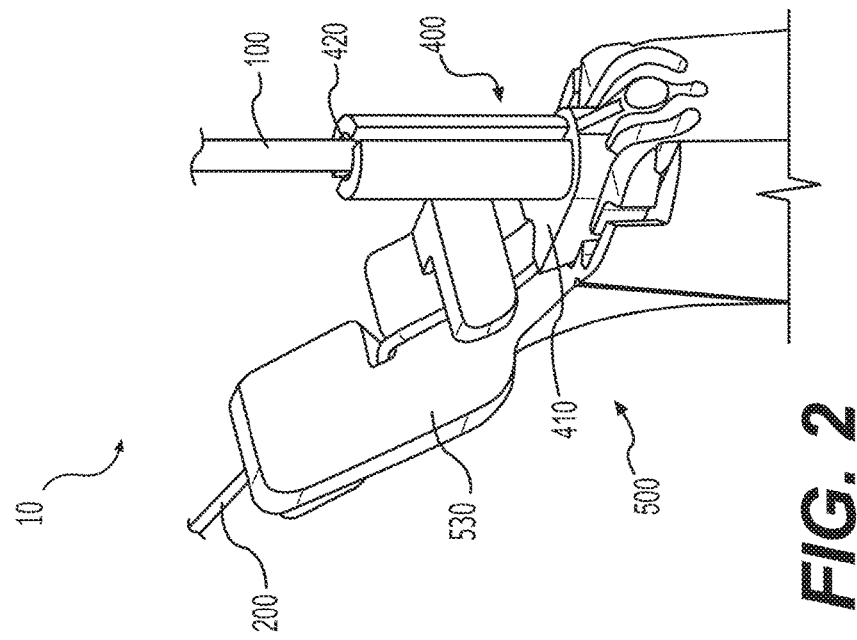
FIG. 3
FIG. 2

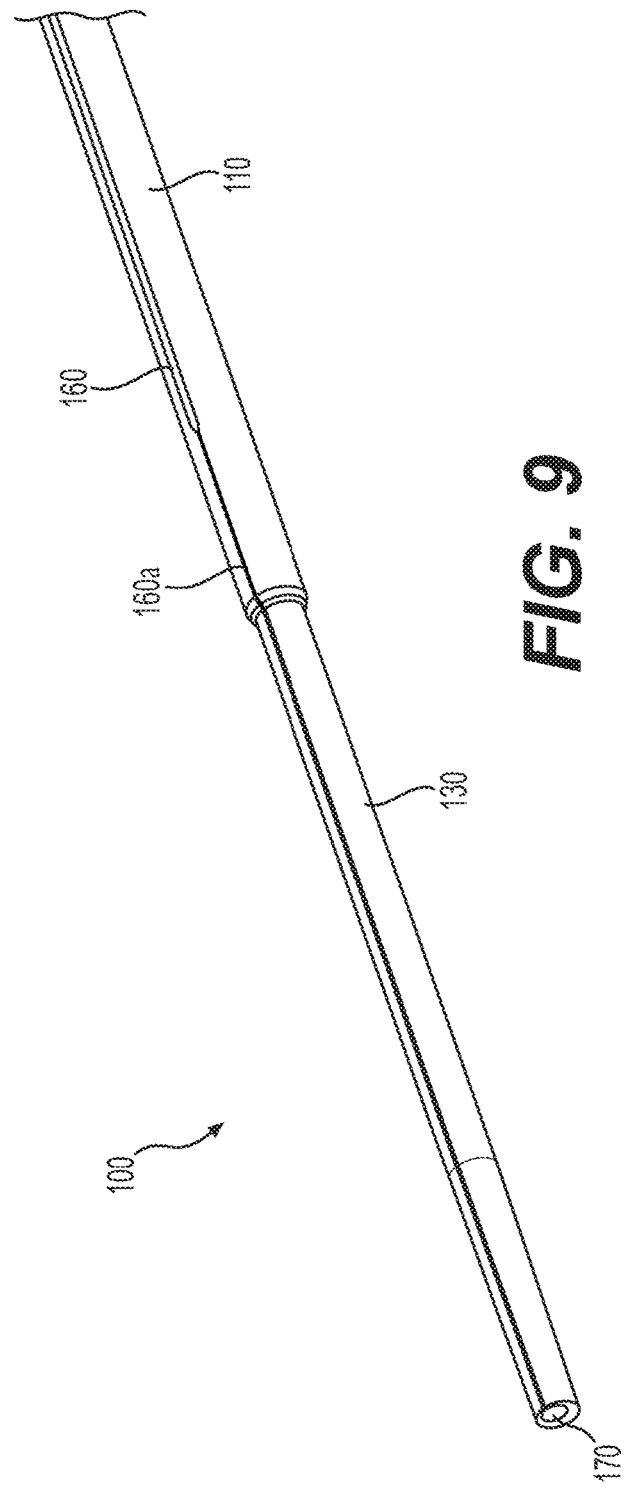
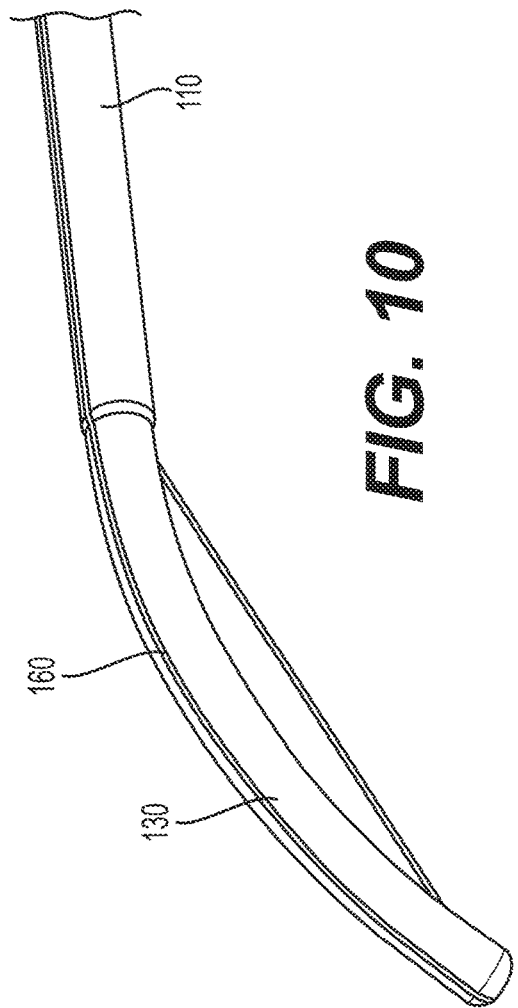

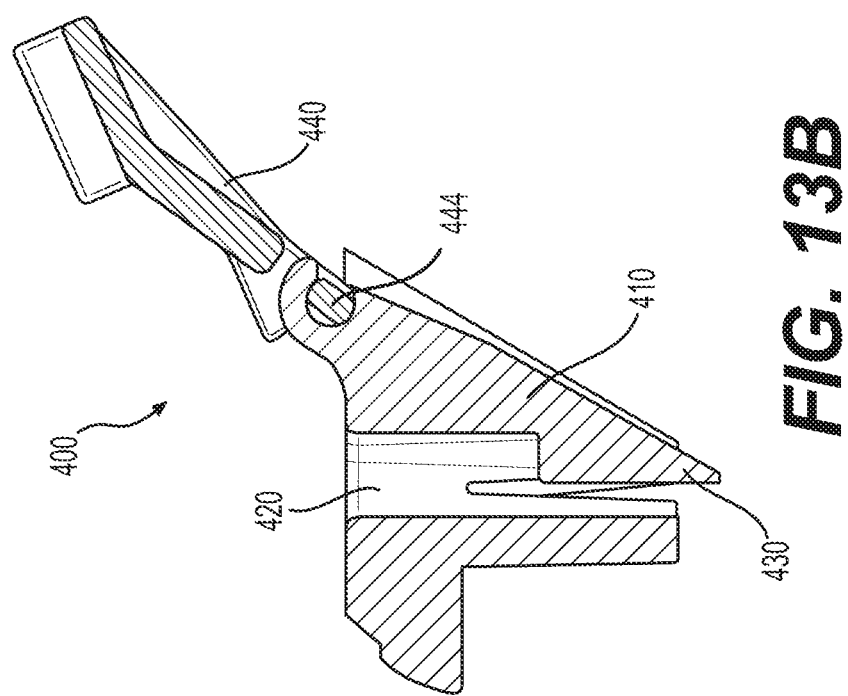
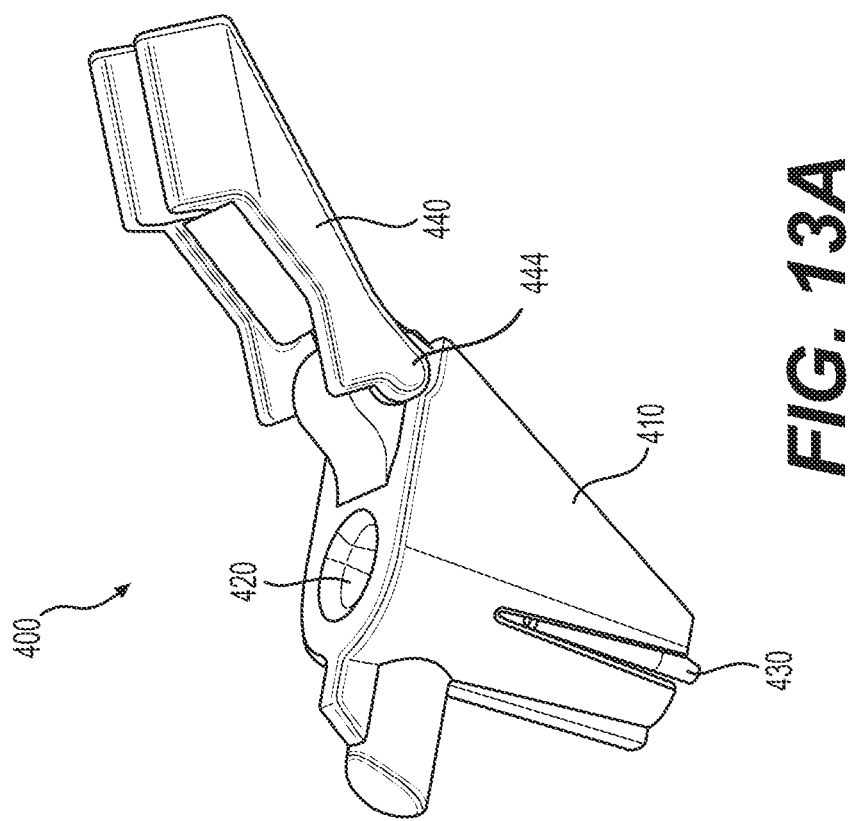

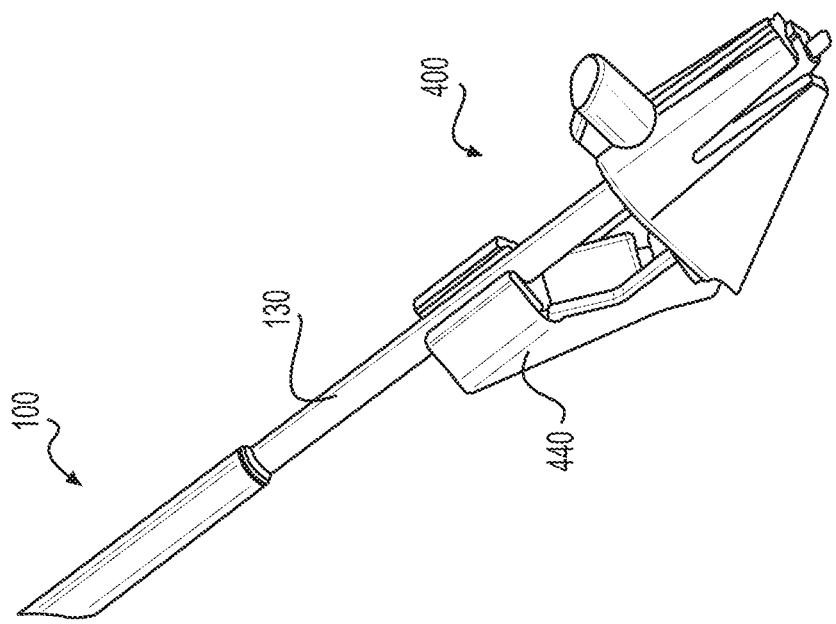
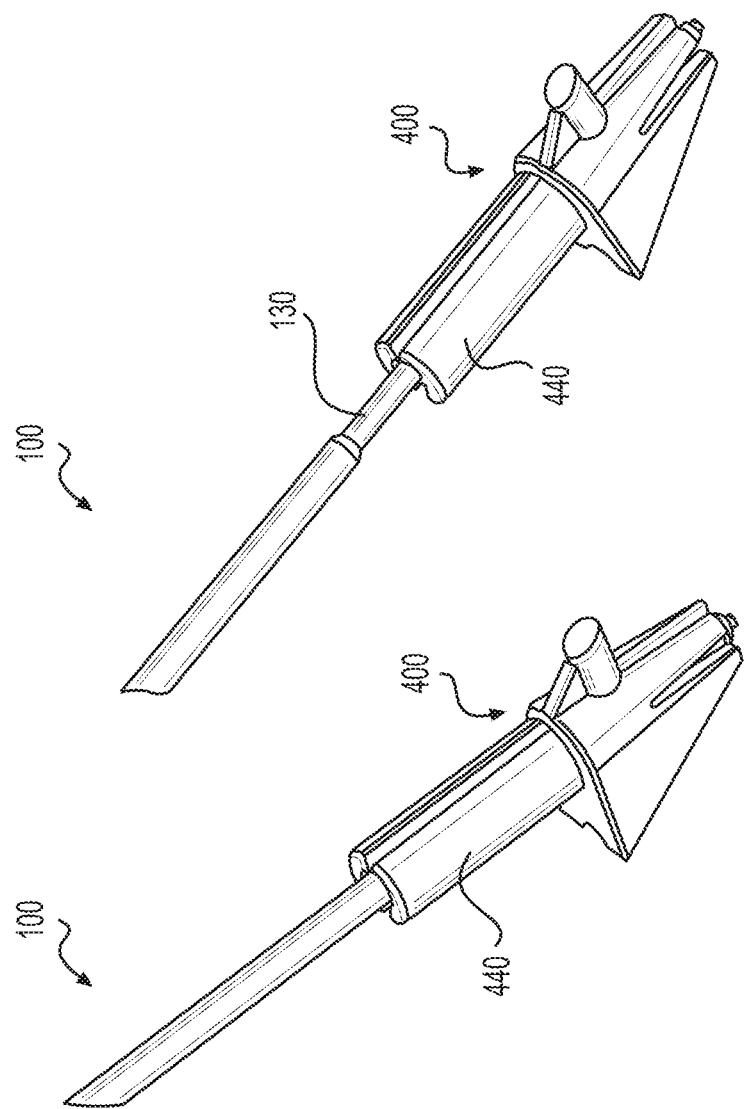
FIG. 14A  FIG. 14B  FIG. 14C

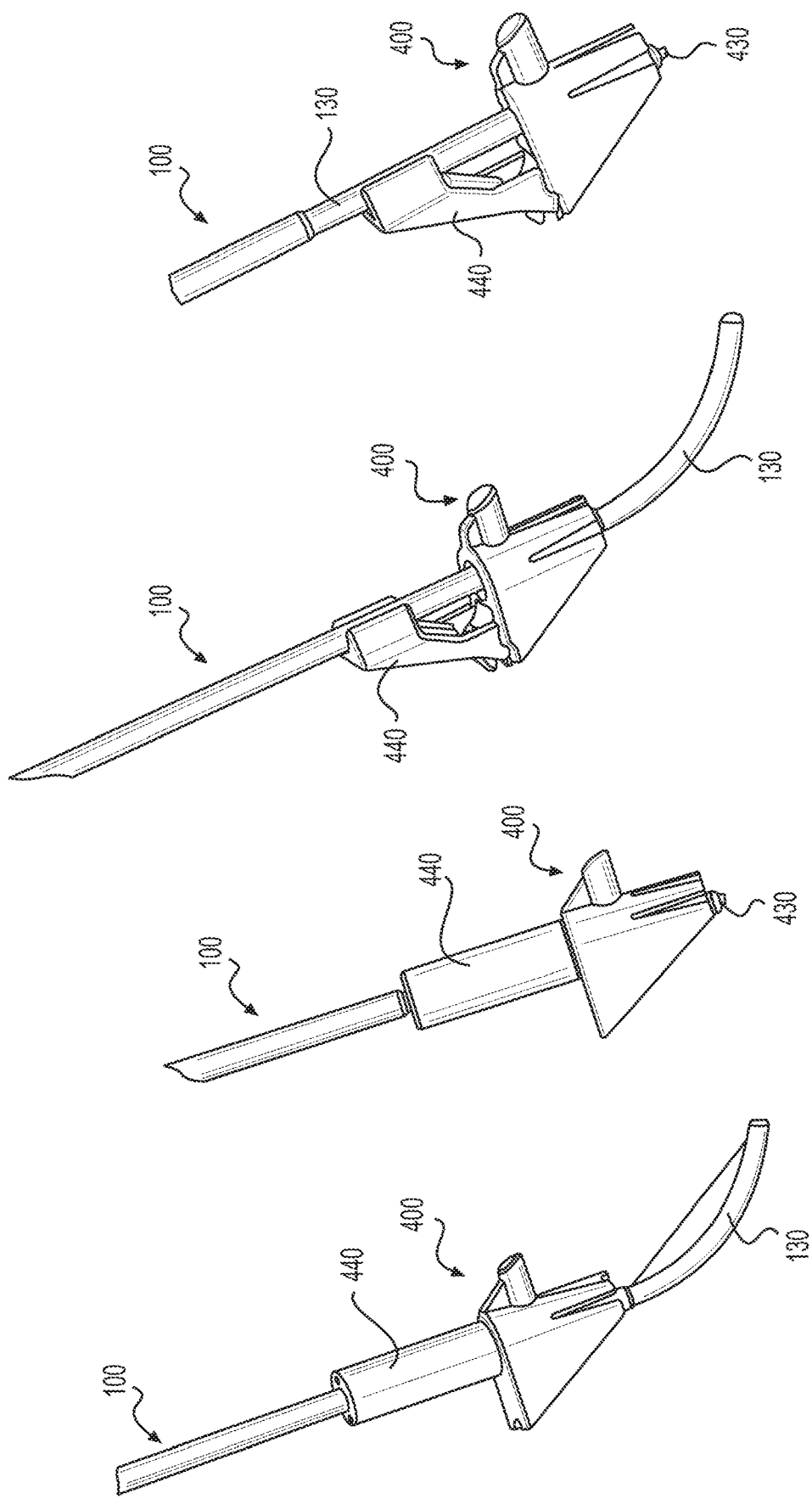

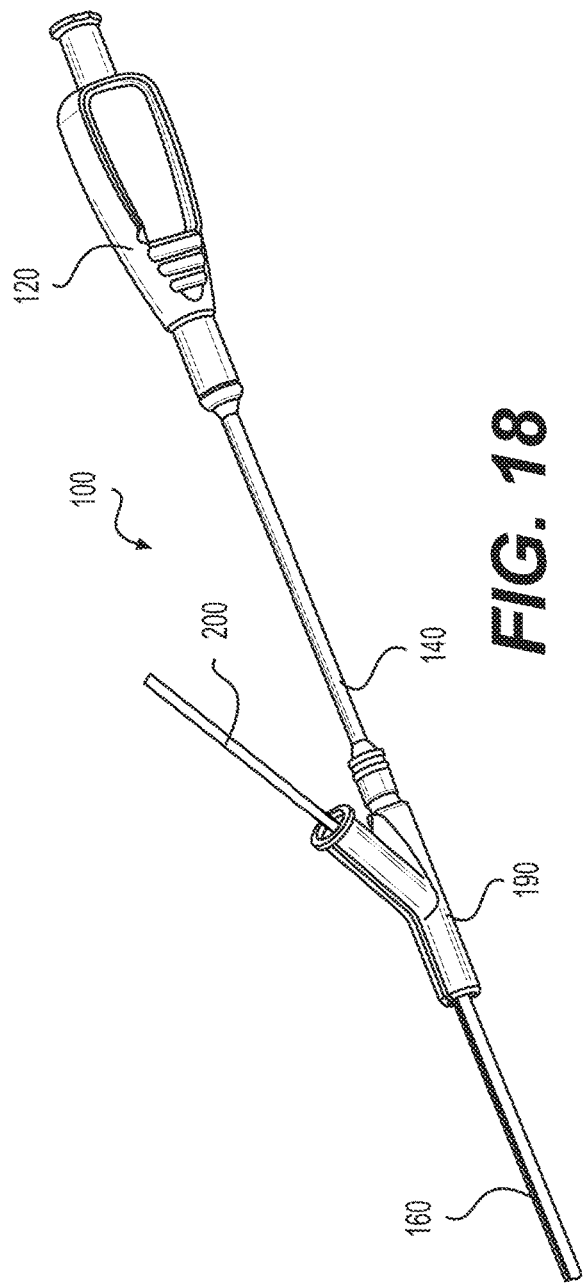
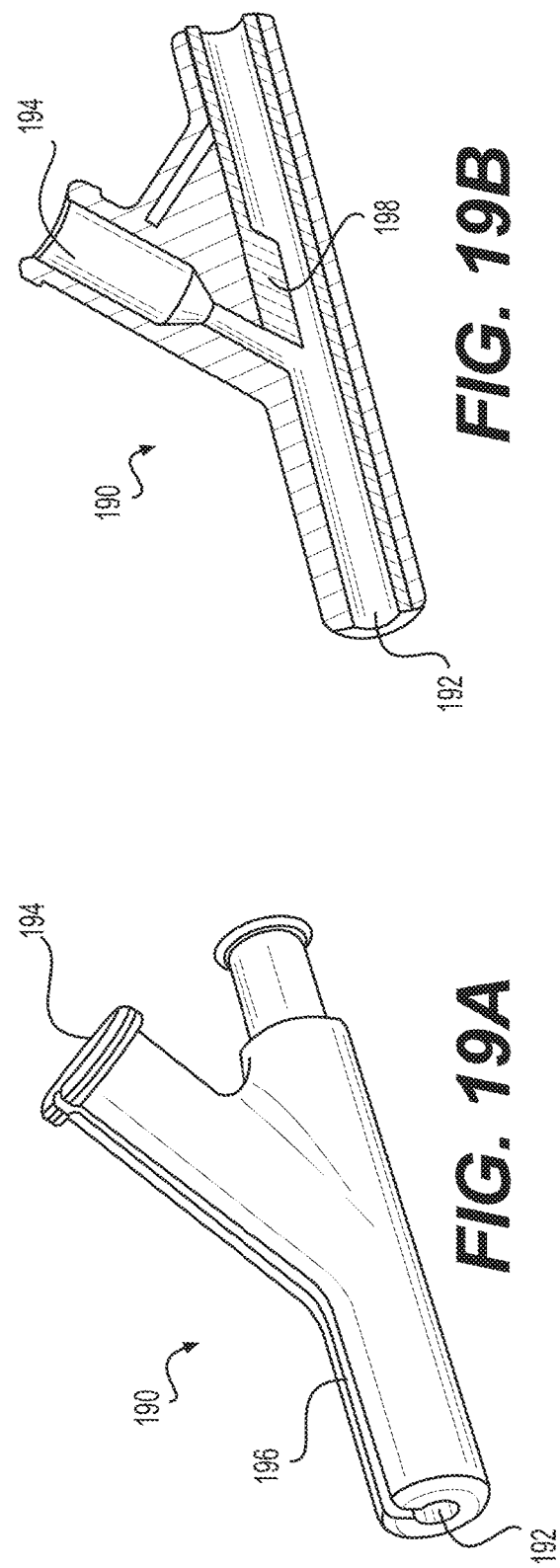

ENDOSCOPIC CANNULATING DEVICES AND METHODS OF USE

BACKGROUND

Technical Field

The present disclosure generally relates to endoscopic cannulating devices and methods of use. More particularly, and without limitation, the disclosed embodiments relate to apparatuses, systems, and methods for introducing or exchanging cannulating devices during an endoscopic procedure.

Background Description

Endoscopic procedures often require the introduction of multiple devices in parallel or in series through the internal lumen of an endoscope. For example, in an endoscopic retrograde cholangiopancreatography (ERCP) procedure, one or more devices need to be introduced into the lumen of a duodenosope to diagnose and treat certain problems of the biliary or pancreatic ductal systems. Typically, an initial operation is performed to introduce a first device through the ampullary orifice (papilla of Vater), and then into the biliary tree until the distal end of the first device is proximate to a desired site in the biliary tree. The first device may be a cannula or a catheter. The initial operation can be diagnostic, such as injecting contrast agents through the device to visualize the biliary tree, or therapeutic, such as enlarging the ampullary orifice.

In many instances, initial visualization could reveal one or more sites in the biliary tree that require further therapeutic operations, such as to remove a stone, open a stricture, or sample tissue at these sites. In such instances, additional devices, such as a sphincterotome, a balloon, a basket, or a stent delivery catheter, may need to be subsequently introduced into the lumen of the duodenoscope to a desired treatment site. In other instances, the one or more devices may be reused and re-introduced to the internal lumen of the endoscope. Thus, to facilitate introducing the subsequent devices to the desired treatment site, a guidewire introduced with the first device is typically held in place in the endoscope to maintain access to the desired treatment site. Removing the first device and introducing the subsequent devices over the guidewire allow for continued access to the desired treatment site for the subsequent devices. However, displacement of the guidewire during this exchange process can result in loss of access to the desired treatment site, which then requires a difficult, time-consuming, and tedious operation to re-direct the guidewire to the desired treatment site.

Two techniques are generally used for endoscopic device exchange. One is termed the "long wire" or "over the wire" technique, and the other is termed the "short wire" technique. The long wire technique uses an extra-long guidewire, whose length is typically longer than the lumen of the endoscope plus the length of the device introduced over the guidewire. In other words, the length of the guidewire extending out of the endoscope needs to be at least as long as that of the device to be replaced. This allows a proximal end of the guidewire to be securely controlled at all times by the physician or an assistant to maintain the position of the guidewire and thus the access to the desired treatment site. To remove the first device off the guidewire, the physician and the assistant must make a series of precise and coordinated maneuvers until the first device is completely off the guidewire. Then, a second device can be introduced over the guidewire through a similarly tedious coordination between the physician and assistant. Throughout this exchange process, the physician lacks or has a limited control of the guidewire, which could result in movement or displacement of the distal end of the guidewire and thus loss of access to the desired treatment site.

To address the shortcomings of the long wire technique, the short wire technique allows the physician to maintain control of the guidewire most of the time during the exchange. In the short wire technique, the guidewire is enclosed in the first device for a short distance from the distal tip to a proximal point of the first device. While the guidewire is held in place, typically by a locking device installed on the biopsy port of the endoscope, a physician can remove the first device by splitting or tearing away the device from the guidewire up to the proximal point of the first device. Then, the physician can perform a short wire exchange for the short distance, which does not require the series of precise coordination between the physician and the assistant as in the long wire exchange. The second device can be introduced by feeding its distal end over the proximal end of the guidewire for the short distance. However, during this short wire exchange, the guidewire is unlocked from the locking device and re-locked after the second device is introduced over the guidewire for the short distance. The locking and unlocking of the guidewire during the short wire exchange still require the physician or the assistant to manually hold the guidewire in place during the device exchange. This is time-consuming and could result in movement or displacement of the distal end of the guidewire and thus loss of access to the desired treatment site.

Therefore, improved apparatuses and devices are needed that allow the guidewire to remain locked in a desired position during the device exchange in an endoscopic procedure. Such apparatuses and devices may be capable of maintaining access to the treatment site during the removal and/or introduction of devices, and may be capable of reducing the time taken for a physician to perform an endoscopic procedure and increasing the effectiveness of the procedure.

SUMMARY

The embodiments of the present disclosure include apparatuses, systems, and methods for introducing or exchanging cannulating devices in an endoscopic procedure. Advantageously, the exemplary embodiments allow a guidewire to be locked in a desired position to maintain access to a desirable treatment site during the device exchange, thereby improving the efficiency and effectiveness of the endoscopic procedure.

According to an exemplary embodiment of the present disclosure, an apparatus for endoscopic operations is described. The apparatus includes a cannulating device to be introduced through an internal lumen of an endoscope via a biopsy port. The cannulating device has an elongated body. The elongated body includes a guidewire lumen configured to receive a guidewire therein, and a slit extending over at least a portion of the length of the elongated body from a distal tip to a proximal position of the elongated body.

According to a further exemplary embodiment of the present disclosure, an apparatus for endoscopic procedures is described. The apparatus includes a cannulating device and an adapter. The cannulating device has an elongated body. The elongated body includes a guidewire lumen configured to receive a guidewire therein, and a slit extending over at least a portion of the length of the elongated body from a distal tip to a proximal position of the elongated body. The adapter is configured to merge the guidewire into the guidewire lumen. The adapter includes an adapter lumen configured to receive the elongated body. The adapter further includes a wedge extending from an inner surface of the adapter lumen. The wedge is configured to widen a portion of the slit such that a portion of the guidewire merges into the guidewire lumen through the widened portion of the slit.

According to a yet further exemplary embodiment of the present disclosure, a method for cannulation is described. The method includes providing a cannulating device having an elongated body comprising a guidewire lumen configured to receive a guidewire therein and a slit extending over at least a portion of the length of the elongated body from a distal tip to a proximal position of the elongated body. The method also includes providing an adapter configured to merge the guidewire into the guidewire lumen. The adapter includes an adapter lumen configured to receive the elongated body and a wedge extending from an inner surface of the adapter lumen. The method further includes receiving the elongated body within the adapter lumen such that the wedge engages and widens a portion of the slit, and merging the portion of a guidewire into the guidewire lumen through the widened portion of the slit.

According to a yet further exemplary embodiment of the present disclosure, an apparatus for endoscopic procedures is described. The apparatus includes means for receiving a cannulating device having a guidewire lumen configured to receive a guidewire therein and a slit extending over at least a portion of the length of the cannulating device. The apparatus further includes means for merging the guidewire into the guidewire lumen.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 2 is a partial perspective view of the exemplary system of FIG. 1, according to embodiments of the present disclosure.

FIG. 3 is a component view of the exemplary system of FIG. 1, according to embodiments of the present disclosure.

FIG. 9 is a perspective view of a distal portion of another exemplary cannulating device, according to embodiments of the present disclosure.

FIG. 10 is a perspective view of a distal portion of another exemplary cannulating device, according to embodiments of the present disclosure.

FIG. 13A is a perspective view of another exemplary adapter in a first position, according to embodiments of the present disclosure.

FIG. 13B is a cross-sectional view of the exemplary adapter of FIG. 13A in the first position, according to embodiments of the present disclosure.

FIG. 14A is a perspective view of a distal portion of the exemplary cannulating device of FIG. 6 with the exemplary adapter of FIGS. 12A-12C, according to embodiments of the present disclosure.

FIG. 14B is a perspective view of a distal portion of the exemplary cannulating device of FIG. 9 with the exemplary adapter of FIGS. 12A-12C, according to embodiments of the present disclosure.

FIG. 14C is a perspective view of a distal portion of the exemplary cannulating device of FIG. 9 with the exemplary adapter of FIGS. 13A-13E, according to embodiments of the present disclosure.

FIG. 15A is a perspective view of a distal portion of the exemplary cannulating device of FIG. 10 with the exemplary adapter of FIGS. 12A-12C, according to embodiments of the present disclosure.

FIG. 15B is a perspective view of a distal portion of the exemplary cannulating device of FIG. 10 with the exemplary adapter of FIGS. 12A-12C, according to embodiments of the present disclosure.

FIG. 15C is a perspective view of a distal portion of the exemplary cannulating device of FIG. 10 with the exemplary adapter of FIGS. 13A-13E, according to embodiments of the present disclosure.

FIG. 15D is a perspective view of a distal portion of the exemplary cannulating device of FIG. 10 with the exemplary adapter of FIGS. 13A-13E, according to embodiments of the present disclosure.

FIG. 18 is a perspective view of a proximal portion of an exemplary cannulating device with an exemplary guidewire port, according to embodiments of the present disclosure.

FIG. 19A is a perspective view of the exemplary guidewire port of FIG. 18, according to embodiments of the present disclosure.

FIG. 19B is a cross-sectional view of the exemplary guidewire port of FIG. 19A, according to embodiments of the present disclosure.

DETAILED DESCRIPTION

Figure 1:
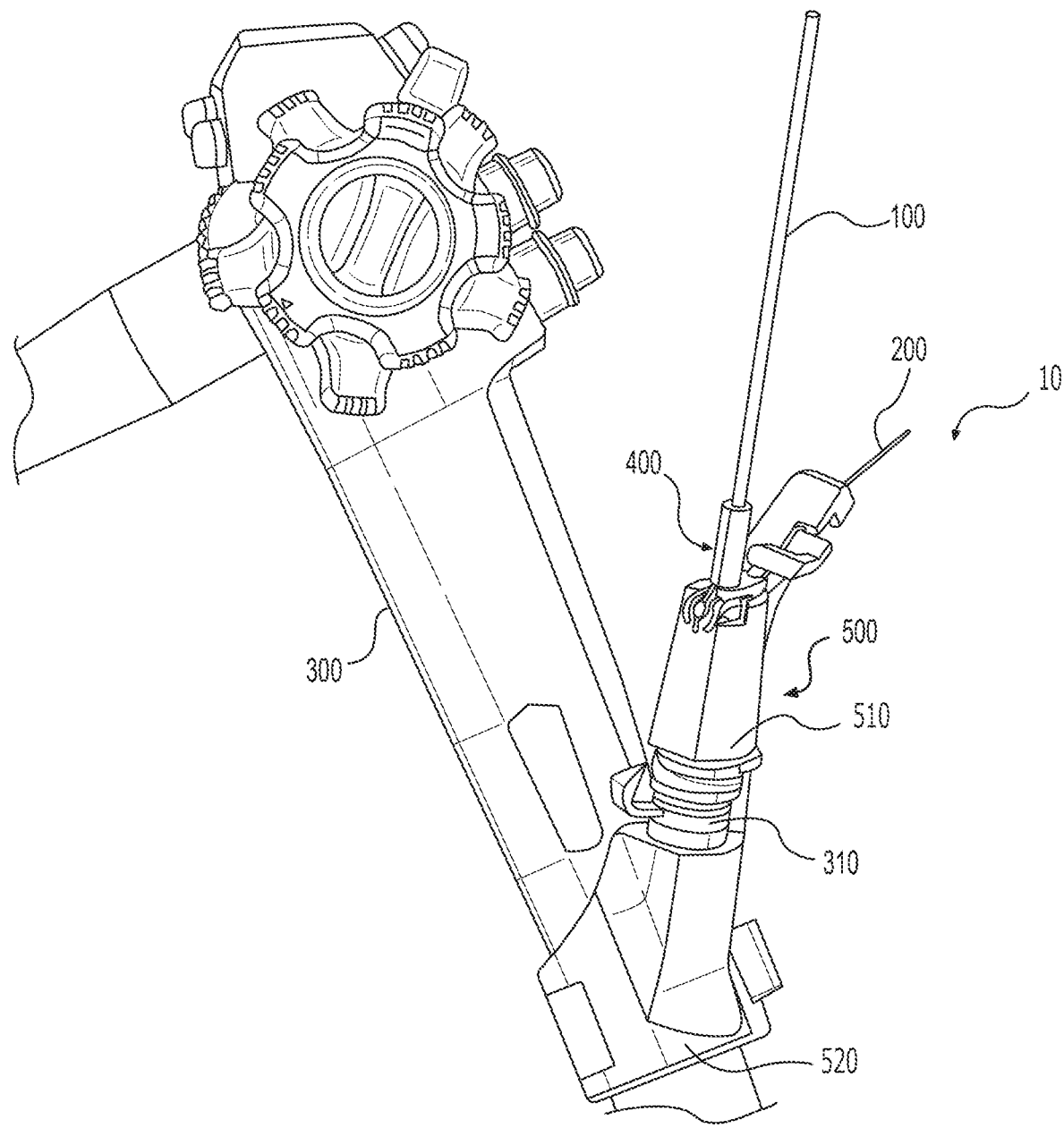
FIG. 1 is a perspective view of an exemplary system for introducing or exchanging endoscopic devices, according to embodiments of the present disclosure.

The disclosed embodiments relate to apparatuses, systems, and methods for efficient and effective device exchange in endoscopic procedures. Embodiments of the present disclosure can be implemented in an endoscopic system for performing suitable diagnostic and/or therapeutic operations to one or more desired treatment sites in the cardiovascular system, the gastrointestinal system, the respiratory system, etc. Advantageously, embodiments of the present disclosure allow for efficient and effective introduction and/or exchange of endoscopic devices through the lumen of an endoscope while maintaining access to at least one desired treatment site during endoscopic procedures.

As described herein, an endoscope typically includes a proximal end and a distal end, and has an internal lumen extending between the distal end and the proximal end. A proximal end may refer to a portion of the endoscope closer to a physician or a medical practitioner. A distal end may refer to a portion of the endoscope closer to a treatment site in the body of a patient during an endoscopic procedure. A device is typically introduced into the internal lumen of the endoscope from a biopsy port at the proximal end towards the distal end of the endoscope until a distal end of the device approximates or reaches a desired treatment site.

According to an aspect of the present disclosure, a device for endoscopic operations may be an endoscopic cannulating device (for example, a cannula or a sphincterotome) to be introduced through an internal lumen of an endoscope. The cannulating device may include an elongated body having a guidewire lumen configured to receive a guidewire therein. The cannulating device may further include a slit extending over at least a portion of the length of the elongated body from a distal tip to a proximal position of the elongated body.

Unlike devices used in the short wire exchange technique, the slit allows the cannulating device to be removed off a guidewire by being split or separated from the guidewire via the slit from a location along the elongated body continuously up to the distal tip. The slit also allows the cannulating device to be introduced over the guidewire by merging with the guidewire via the slit from its distal tip continuously until a distal end of the cannulating device reaches the desired treatment site. Advantageously, during the device exchange, the guidewire can remain locked in a desired position by a locking device, thereby eliminating the need to manually holding the guidewire by a physician to maintain a previously obtained access to the desired treatment site.

As described herein, a distal tip of the cannulating device refers to the furthest distal location along the cannulating device. A distal end or a distal portion of the cannulating device refers to a section of the device extending from the distal tip over a predetermined length. A proximal point of the cannulating device refers to a location along the elongated body closer to a physician or a medical practitioner. A proximal end or a proximal portion of the cannulating device refers to a section of the device extending over a predetermined length near the proximal point.

In some embodiments, a natural width of the slit of the cannulating device may be substantially smaller than the diameter of the guidewire. To introduce a cannulating device over the guidewire, a portion of the slit is opened or widened, allowing a portion of the guidewire to merge into a portion of a cannulating device. The opened portion of the slit then returns to its natural width after the merge. In some instances, after merging into the cannulating device, the guidewire is received by a partially enclosed guidewire lumen extending across the longitudinal axis of the cannulating device. Advantageously, the transient widening and narrowing of the slit allows the introduction of the cannulating device over the guidewire as well as retaining the guidewire within the cannulating device during an endoscopic operation after the device exchange.

The natural width of the slit of a distal portion of the cannulating device may be smaller than that of the remaining portion of the cannulating device. The narrower slit at the distal portion advantageously allows the guidewire to be retained in the guidewire lumen even when the distal portion undergoes deformation, the bending of the distal portion of a sphincterotome, for example.

In some embodiments, the outer diameter of the elongated body of the cannulating device is substantially uniform along its length. In other embodiments, the outer diameter of a distal end of the elongated body is smaller than that of the remaining portion of the elongated body. The length of the distal end of may be shorter than the length of a distal portion of the cannulating device where the natural width of the slit is narrower. In such instances, the portion of the slit having a narrower natural width may extend longer than the distal end of the cannulating device having the smaller outer diameter.

In some embodiments, the elongated body of the cannulating device may further include an opening where the guidewire enters or exits from the guidewire lumen. For example, to load a guidewire in the cannulating device, the guidewire may be introduced into the guidewire lumen of the cannulating device through the opening. Also, after merging into the guidewire lumen from the distal tip of the cannulating device, the guidewire may exit from the guidewire lumen at the opening.

The opening may be located near or closer to a distal end of the cannulating device such that only a short portion of the guidewire is retained in the guidewire lumen. Alternatively, the opening may be located near or closer to a proximal end of the cannulating device such that a substantial portion of the guidewire is retained in the guidewire lumen. In such instances, the opening may reside outside of the internal lumen of the endoscope after the introduction of the cannulating device. The cannulating device may further include a guidewire port attached to the elongated body at the opening. The guidewire port may facilitate the introduction of the guidewire into the guidewire lumen by a physician or medical practitioner.

According to an aspect of the present disclosure, an apparatus for endoscopic procedures may include an adapter that allows for the introduction of the cannulating device over a guidewire. The adapter may include an adapter lumen for receiving the cannulating device. The adapter may further include a wedge extending from an inner surface of the adapter lumen. As the cannulating device passes through the adapter lumen, the wedge may wedge open or widen a portion of the slit of the cannulating device, allowing a portion of the guidewire to merge into a corresponding portion of the cannulating device through the widened portion of the slit. After passing by the wedge, the widened portion of the slit may return to its natural width, allowing the merged portion of the guidewire to be retained in the cannulating device, e.g., in the guidewire lumen of the cannulating device.

The adapter can merge the guidewire into the cannulating device as the cannulating device passes through the adapter lumen continuously from a distal tip of the cannulating device until it reaches a desired treatment site. Advantageously, during this continuous merging of the guidewire into the cannulating device, rather than being unlocked and manually held in place, the guidewire can remain locked in a desired position, thereby reducing the risk of displacement of the guidewire and thus the risk of losing access to the desired treatment site.

In some embodiments, the adapter include a holder configured to hold at least a portion of the elongated body as the cannulating device passes through the adapter lumen. The holder may use any suitable form that allows the cannulating device to be introduced over a guidewire fixed in place in a steady fashion. For example, the holder may include a channel or a clamping structure that frictionally holds a portion of the elongated body while not hindering its passage through the adapter lumen.

According to another aspect of the present disclosure, the apparatus for endoscopic procedures may include an endoscopic block to be affixed to a biopsy port of an endoscope. The endoscopic block may include a main channel configured to receive at least one guidewire. The endoscopic block may fixedly or removably engage with the adapter to introduce a cannulating device over a guidewire received in the main channel. A cannulating device passing through the adapter lumen would align with and merges with the guidewire in the main channel of the endoscopic block. Advantageously, the use of the endoscopic block and the adapter for introducing a cannulating device over a guidewire eliminates the need to perform a long wire or short wire exchange, thereby improving the efficiency and accuracy of device exchange during an endoscopic procedure.

In some embodiments, the endoscopic block may further include a locking device for fixing a guidewire in a desired position. The desired position may be predetermined after an initial operation before performing the device exchange. For example, the locking device may include zigzag locking features that retain the guidewire in the predetermined desired position by frictionally holding the guidewire in place. The zigzag locking features may be used in combination with other mechanical features that can bend, twist, pinch, clamp, or lock the guidewire in place.

The endoscopic block may include more than one locking devices for locking one or more additional guidewires. The locking devices may use the same or different locking features and/or mechanisms. Each guidewire may be locked or unlocked from the locking features of the locking devices independently, and may be merged into a different cannulating device. The ability to receive and lock more than one guidewires advantageously provides a physician more flexibility in selecting and using a suitable number and types of devices for conducting medical operations during an endoscopic procedure.

Reference will now be made in detail to embodiments and aspects of the present disclosure, examples of which are illustrated in the accompanying drawings. Where possible, the same reference numbers will be used throughout the drawings to refer to the same or like parts.

FIG. 1 is a perspective view of an exemplary system 10 for introducing or exchanging endoscopic devices. As shown in FIG. 1, system 10 may include a cannulating device 100 to be introduced over a guidewire 200 through an internal lumen (not shown) of an endoscope 300 (partially shown) via a biopsy port 310. Port 310 may be normally closed by a biopsy valve before use. System 10 may further include an adapter 400 and an endoscopic block 500.

Adapter 400 may be fixedly or removably engaged with endoscopic block 500 and is configured to receive cannulating device 100. Endoscopic block 500 includes a main body portion 510 and a fastener 520 that affixes endoscopic block 500 to port 310 of endoscope 300.

FIG. 2 is a partial perspective view of system 10 and FIG. 3 is a component view of system 10. As shown in FIGS. 2 and 3, adapter 400 includes a body 410, an adapter lumen 420, and a wedge 430 (partially shown). Body 410 can be received by an opening of endoscopic block 500. For example, body 410 may be removably or fixedly engaged with the opening of endoscopic block 500 via frictional fit, threaded fit, snap fit, etc., thereby securing adapter 400 on endoscopic block 500. Adapter lumen 420 extends through body 410 for receiving cannulating device 100. Wedge 430 may align with a longitudinal axis of adapter lumen 420 such that when cannulating device 100 passes though adapter lumen 420, a slit (not shown) extending along cannulating device 100 would pass by wedge 430. Wedge 430 may widen the slit of cannulating device 100 as it passes by, as described further below in reference to FIGS. 6 and 7.

As shown in FIGS. 2 and 3, endoscopic block 500 further includes a locking device 530 for fixing guidewire 200 in a desired position. Locking device 530 may fix guidewire 200 in place, by frictionally pinching, grapping, clamping, or locking guidewire 200. For example, as shown in FIGS. 2 and 3, locking device 530 may include zigzag locking features that fix guidewire 200 in a desired position by frictionally maintaining guidewire 200 in place. The fixing of guidewire 200 allows the distal end of cannulating device 100 that is introduced over guidewire 200 to approximate or reach a desired treatment site maintained by the distal end of guidewire 200. As described herein, endoscopic block 500 may include more than one locking devices 530 for holding more than one guidewires 200 in place. Alternatively, one locking device 530 may hold more than one guidewires 200 in place.

Figure 4A:
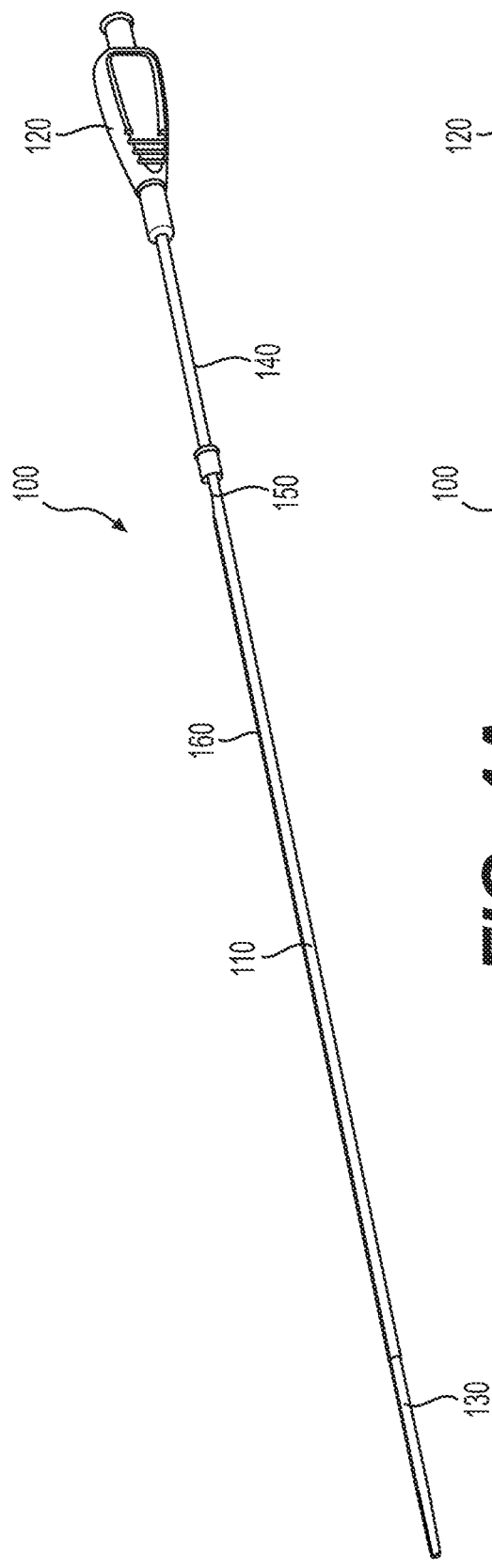
FIG. 4A is a perspective view of an exemplary cannulating device, according to embodiments of the present disclosure.
Figure 4B:
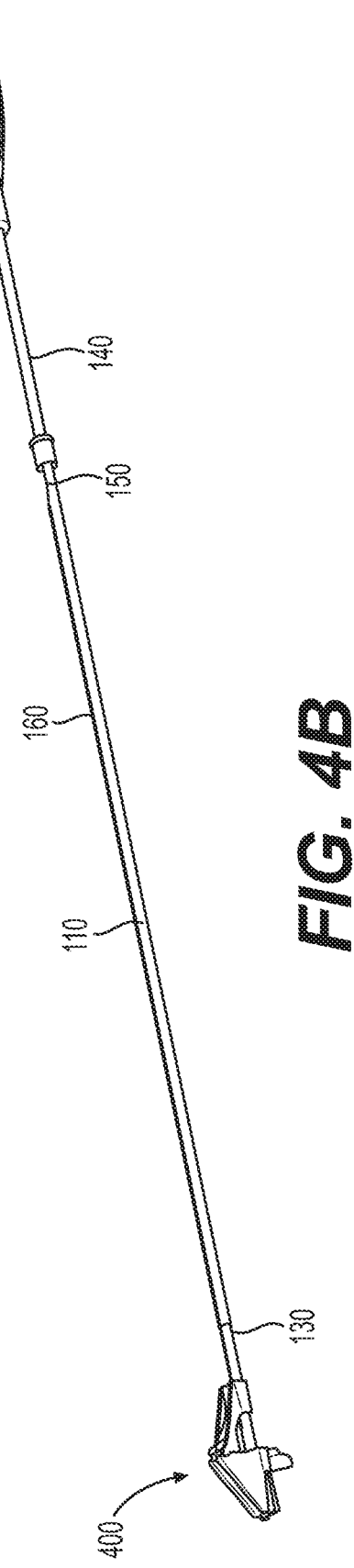
FIG. 4B is a perspective view of the exemplary cannulating device of FIG. 4A loaded with an exemplary adapter, according to embodiments of the present disclosure.
Figure 5A:
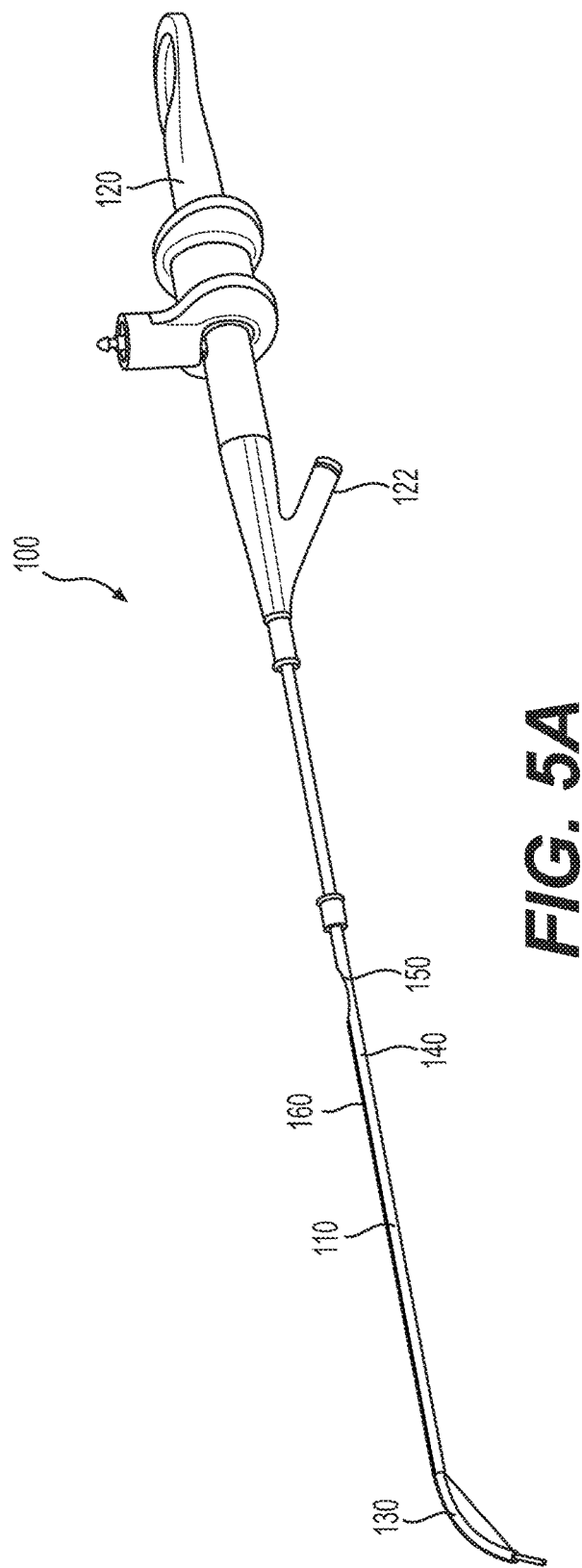
FIG. 5A is a perspective view of another exemplary cannulating device, according to embodiments of the present disclosure.
Figure 5B:
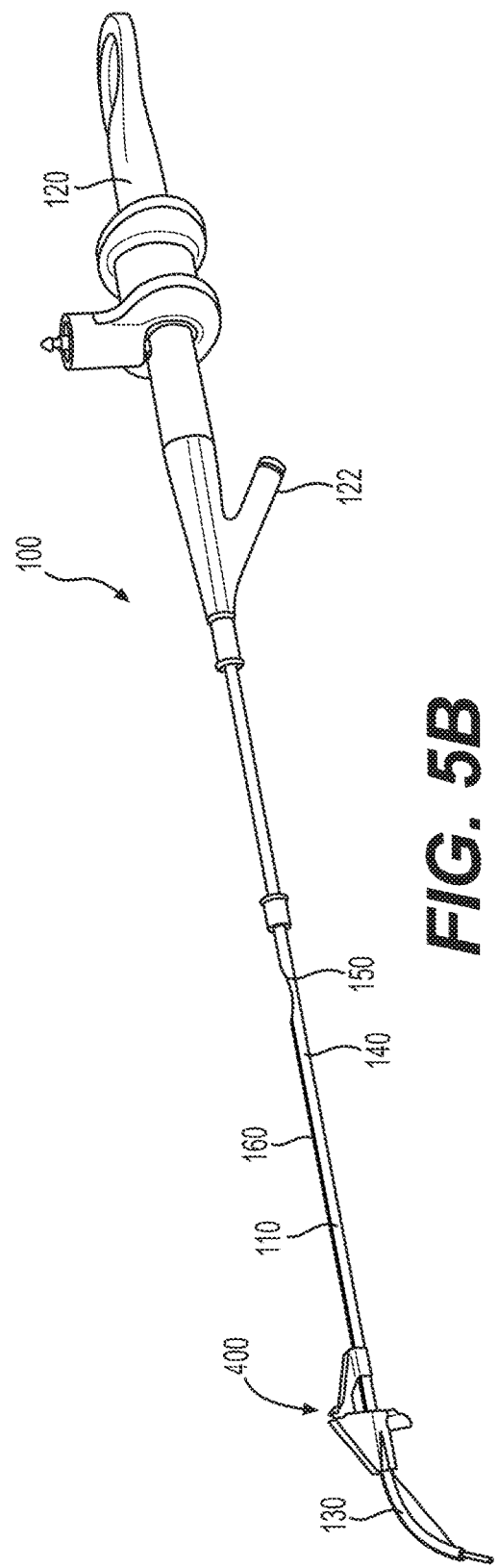
FIG. 5B is a perspective view of the exemplary cannulating device of FIG. 5A loaded with an exemplary adapter, according to embodiments of the present disclosure.

FIG. 4A is a perspective view of an exemplary cannulating device 100 and FIG. 4B is a perspective view of the exemplary cannulating device of FIG. 4A loaded with an exemplary adapter 400. FIG. 5A is a perspective view of another exemplary cannulating device 100 and FIG. 5B is a perspective view of the exemplary cannulating device of FIG. 5A loaded with the exemplary adapter 400. Cannulating device 100 may be an endoscopic catheter as shown in FIGS. 4A and 4B or may be an endoscopic sphincterotome as shown in FIGS. 5A and 5B. When cannulating device 100 is an endoscopic sphincterotome, cannulating device 100 may further include a side port 122 for injecting a contrast agent, for example. Additionally, cannulating device 100 may be provided for use by a physician or medical practitioner by itself as shown in FIGS. 4A and 5A or loaded with adapter 400 as shown in FIGS. 4B and 5B.

As shown in FIGS. 4A-5B, cannulating device 100 may include an elongated body 110 and a handle 120. Elongated body 110 includes a distal end 130 and a proximal end 140. Cannulating device 100 may further include an opening 150 where guidewire 200 (not shown in FIGS. 4A-5B) enters or exits from a guidewire lumen (not shown in FIGS. 4A-5B) of cannulating device 100.

Figure 6:
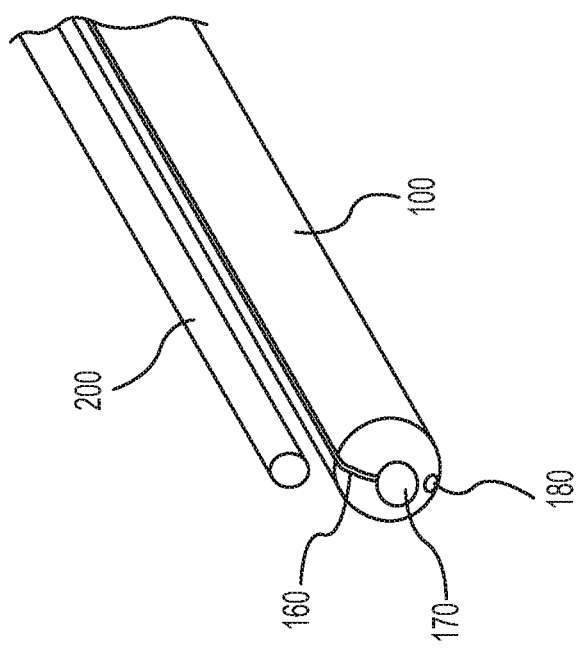
FIG. 6 is a partial perspective view of an exemplary guidewire and an exemplary cannulating device, according to embodiments of the present disclosure.

FIG. 6 is a partial perspective view of guidewire 200 juxtaposed with cannulating device 100. As shown in FIGS. 4A-6, cannulating device 100 includes a slit 160 and a partially enclosed guidewire lumen 170 connected to slit 160. Guidewire lumen 170 may have the same length as slit 160. In some embodiments, lumen 170 and slit 160 may extend over a predetermined length from a distal tip to a proximal position of cannulating device 100. In other embodiments, lumen 170 and slit 160 may extend over a predetermined length from a distal tip to a distal position of cannulating device 100. As described herein, a proximal position or a proximal point of cannulating device 100 refers to a location along elongated body 110 closer to a physician or a medical practitioner. A distal position or a distal point of cannulating device 100 refers to a location along elongated body 110 closer to the distal end of cannulating device 100.

Guidewire 200 can be merged into guidewire lumen 170 through slit 160. In addition, slit 160 allows cannulating device 100 to be removed off guidewire 200 that has been merged into guidewire lumen 170 by being split or separated from guidewire 200 via slit 160. In some embodiments, as shown in FIG. 6, cannulating device 100 may include at least one additional inner lumen 180 for receiving a secondary device (not shown) or for injecting fluids such as contrast to perform a medical operation. The secondary device may be introduced into cannulating device 100 before or after it is merged with guidewire 200.

As shown in FIG. 6, the diameter of guidewire 200 is substantially greater than a natural width of slit 160. This allows guidewire 200 to be retained within guidewire lumen 170 of cannulating device 100 after merging into guidewire lumen 170 to effectively guide cannulating device 100 to desired treatment sites. However, to merge guidewire 200 into guidewire lumen 170 of cannulating device 100 through slit 160, the width of slit 160 needs to be temporarily enlarged for guidewire 200 to enter as described below.

Figure 7:
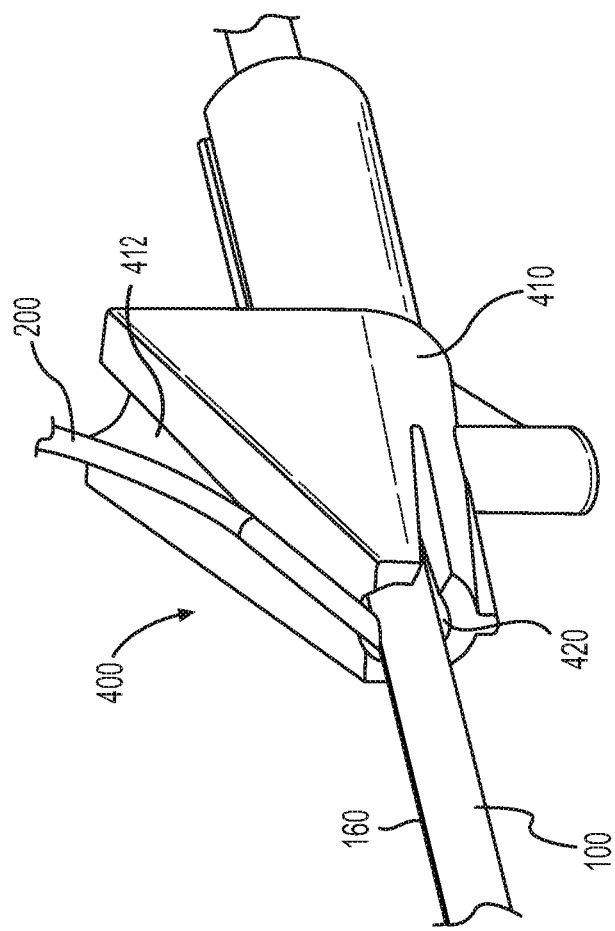
FIG. 7 is a partial perspective view of an exemplary adapter for merging the exemplary guidewire of FIG. 6 into the exemplary cannulating device of FIG. 6, according to embodiments of the present disclosure.

FIG. 7 illustrates the use of adapter 400 for merging guidewire 200 into cannulating device 100 through slit 160. As shown in FIG. 7, when cannulating device 100 passes through adapter lumen 420, cannulating device 100 passes by wedge 430 (not shown), which widens a portion of slit 160 to receive the nearby portion of guidewire 200 received through a groove 412. This temporary widening of slit 160 allows guidewire 200 to be merged into guidewire lumen 170 of cannulating device 100.

As described herein, adapter 400 may have any suitable geometry and/or mechanical features to be securely fit into endoscopic block 500 and/or to merge guidewire 200 into cannulating device 100. Exemplary embodiments and/or features of adapter 400 are described further below in reference to FIGS. 11A-13E.

Figure 8B:
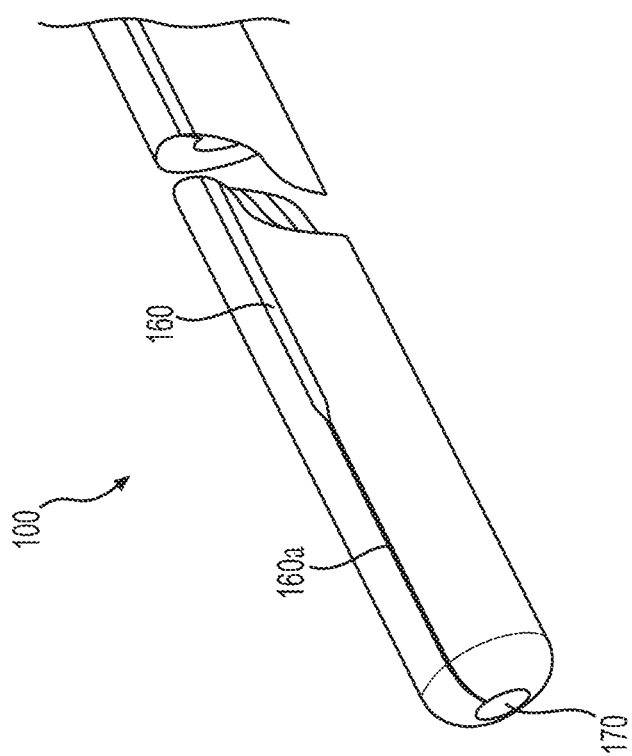
FIG. 8B is a partial perspective view of another exemplary cannulating device, according to embodiments of the present disclosure.
Figure 8A:
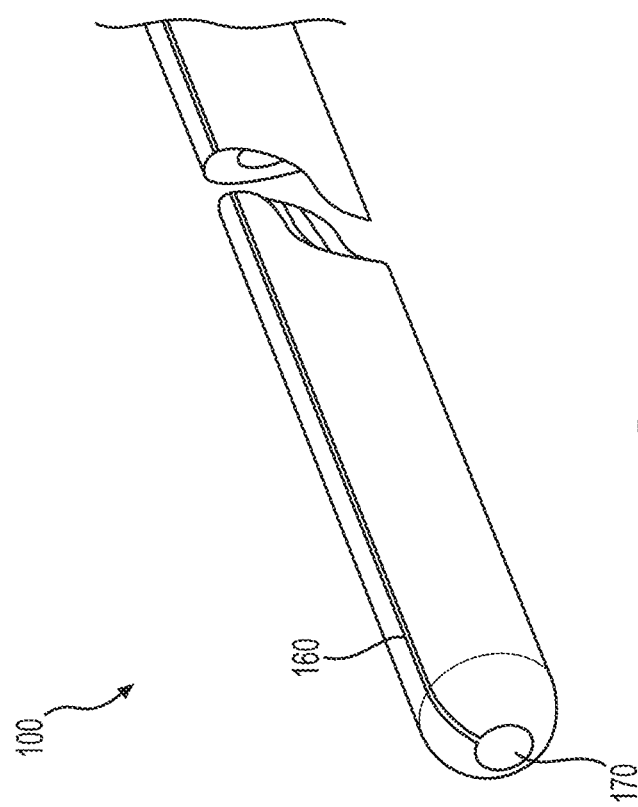
FIG. 8A is a partial perspective view of an exemplary cannulating device, according to embodiments of the present disclosure.

FIGS. 8A and 8B are partial perspective views of exemplary embodiments of cannulating device 100. In some embodiments, as shown in FIG. 8A, the natural width of slit 160 remains substantially the same across its length extending over cannulating device 100. In other embodiments, as shown in FIG. 8B, the natural width of slit 160 is narrower for a distal portion of cannulating device 100 than that of the remaining portion of cannulating device 100. This narrower slit portion (shown as slit portion 160a in FIG. 8B) further restricts guidewire 200 from thrusting out of guidewire lumen 170 of the distal portion when it undergoes deformation during an endoscopic procedure, such as bending or curving.

FIGS. 9 and 10 are perspective views of distal portions of exemplary embodiments of cannulating devices 100. In some embodiments, as shown in FIG. 9, the outer diameter of a distal end 130 of cannulating device 100 is smaller than that of the remaining portion of cannulating device 100. For example, distal end 130 may extend from an angled narrowing or a neckdown of elongated body 110 to the distal tip of cannulating device 100. In the instances where cannulating device 100 is an endoscopic sphincterotome, distal end 130 is the bendable portion of the endoscopic sphincterotom. In these instances, as shown in FIG. 9, the narrower slit portion 160a may extend across or beyond the length of distal end 130.

Exemplary embodiments and/or features of adapter 400 for introducing cannulating device 100 over guidewire 200 are described below in reference to FIGS. 11A-13E.

Figure 11C:
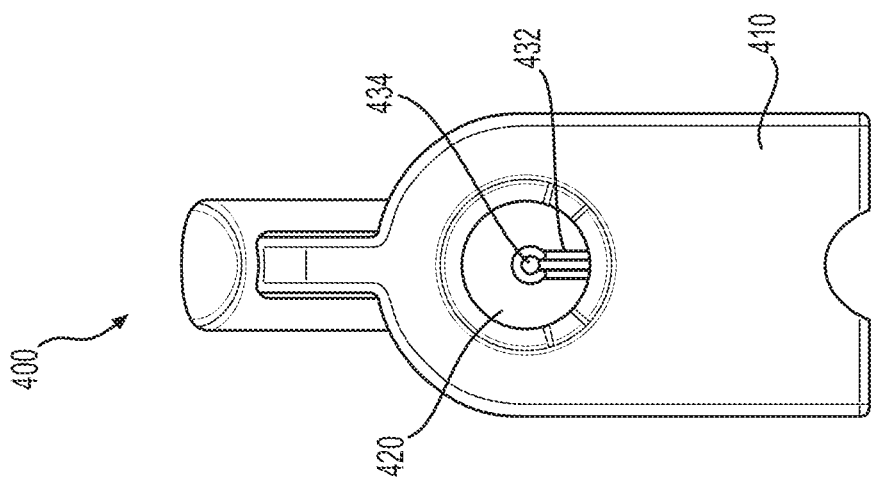
FIG. 11C is a top plan view of the exemplary adapter of FIG. 11A, according to embodiments of the present disclosure.
Figure 11B:
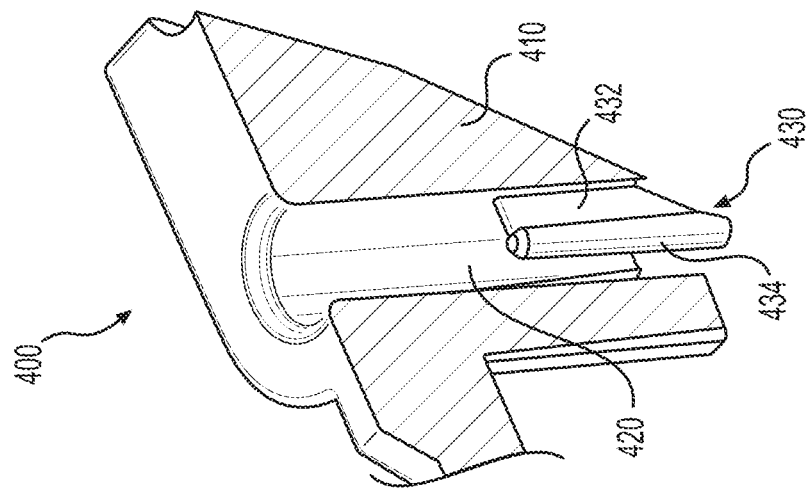
FIG. 11B is a cross-sectional view of the exemplary adapter of FIG. 11A, according to embodiments of the present disclosure.
Figure 11A:
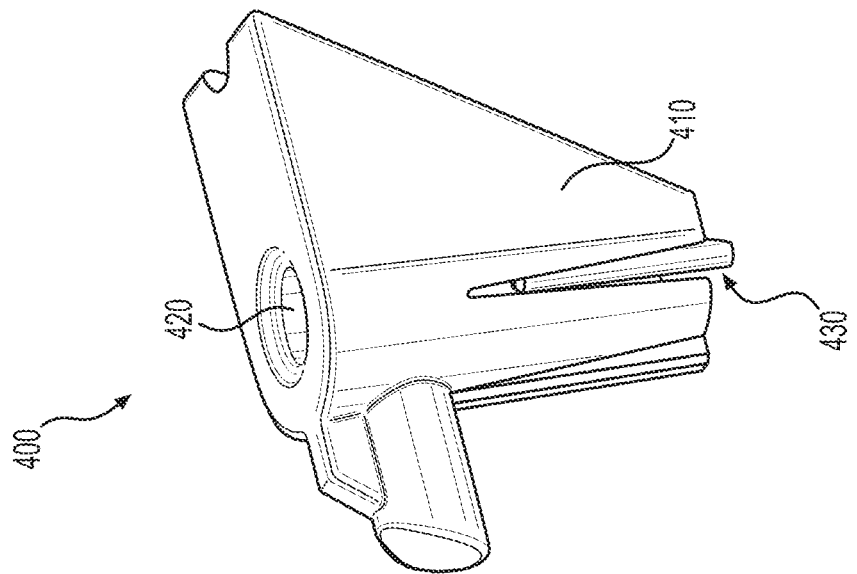
FIG. 11A is a perspective view of an exemplary adapter, according to embodiments of the present disclosure.

FIG. 11A is a perspective view of an exemplary adapter 400. FIG. 11B is a cross-sectional view of the exemplary adapter 400 of FIG. 11A. FIG. 11C is a top plan view of the exemplary adapter of FIG. 11A. As shown in FIGS. 2, 3, and 11A-11C, adapter 400 includes body 410, adapter lumen 420, and wedge 430. Adapter lumen 420 extends through body 410. Wedge 430 extends from an inner surface of adapter lumen 420 towards a longitudinal axis of adapter lumen 420. As described herein, the longitudinal axis may be the center axis or an off-center axis of adapter lumen 420. In some embodiments, as shown in FIG. 11B, wedge 430 extends along the longitudinal axis of adapter lumen 420 over a short distance. In other embodiments, wedge 430 extends across the length of adapter lumen 420 (not shown).

As shown in FIGS. 11B and 11C, wedge 430 may include a wedge portion 432 and a guide portion 434. Wedge portion 432 may be a thin plate, such as a fin-shaped plate, that stems from the inner surface of adapter lumen 420. Wedge portion 432 may extend up to the longitudinal axis of adapter lumen 420, where it is connected with guide portion 434. Guide portion 434 may have a tapered elongated shape that aligns with the longitudinal axis of adapter lumen 420.

When cannulating device 100 is initially inserted through adapter lumen 420, the distal tip of cannulating device 100 passes by wedge 430. Wedge portion 432 opens up or widens a portion of slit 160 of cannulating device 100, thereby allowing guidewire 200 to merge into slit 160. Wedge portion 432 further maintains the opening of slit 160 as cannulating device 100 passes by wedge 430, thereby allowing for continuous merging of guidewire 200 into slit 160. Guide portion 434 enters guidewire lumen 170 of cannulating device 100 to maintain the direction of insertion of cannulating device 100 during its merge with guidewire 200. After the widened portion of slit 160 passes by wedge 430 and merges with a portion of guidewire 200, it returns to its natural width out of its own elasticity. The merged portion of guidewire 200 is then retained in guidewire lumen 170 of cannulating device 100.

Figure 12C:
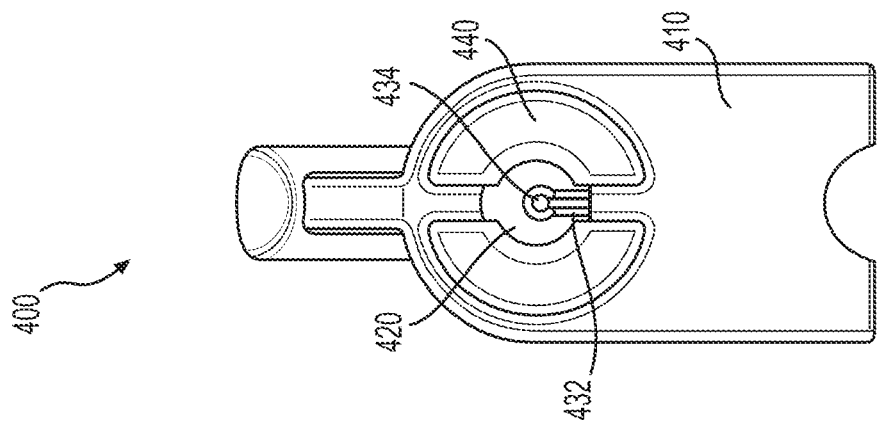
FIG. 12C is a top plan view of the exemplary adapter of FIG. 12A, according to embodiments of the present disclosure.
Figure 12B:
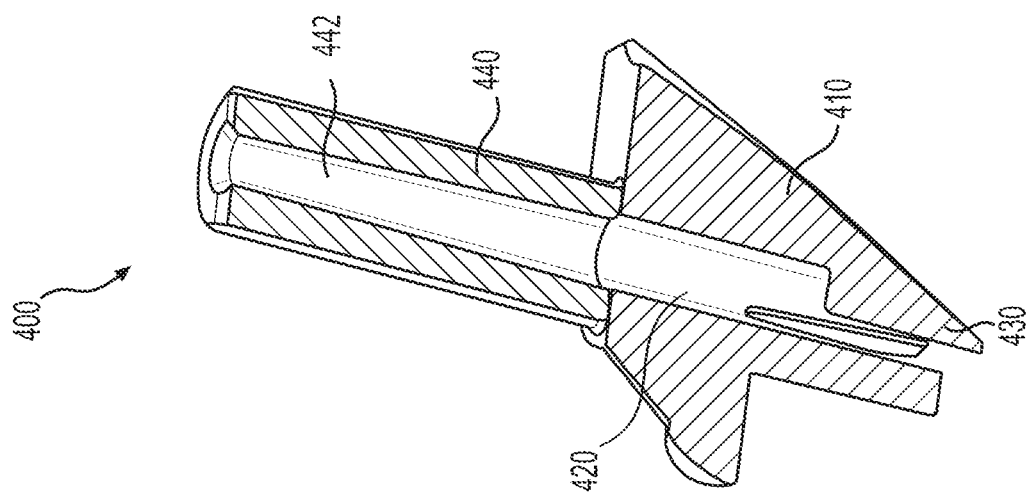
FIG. 12B is a cross-sectional view of the exemplary adapter of FIG. 12A, according to embodiments of the present disclosure.
Figure 12A:
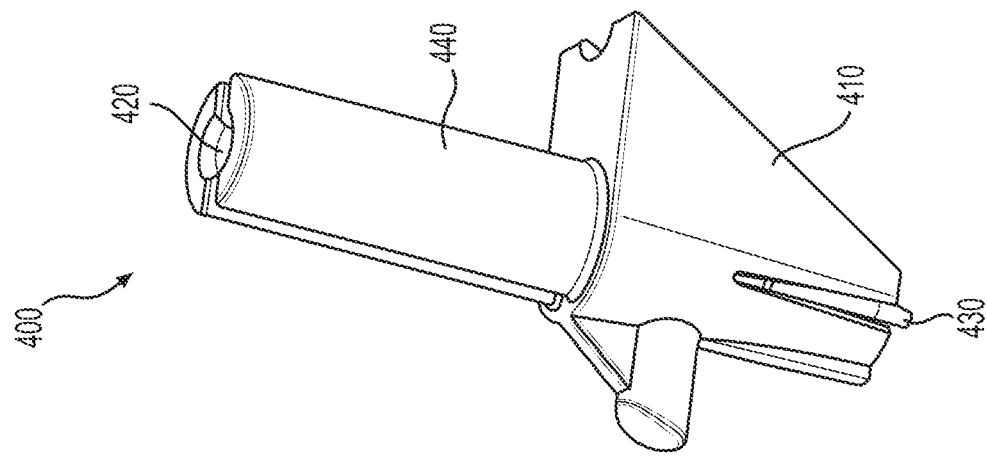
FIG. 12A is a perspective view of another exemplary adapter, according to embodiments of the present disclosure.

FIG. 12A is a perspective view of another exemplary adapter 400. FIG. 12B is a cross-sectional view of the exemplary adapter 400 of FIG. 12A. FIG. 12C is a top plan view of the exemplary adapter of FIG. 12A. As shown in FIGS. 12A-12C, in some embodiments, adapter 400 further includes a holder 440. When cannulating device 100 passes through adapter lumen 420, holder 440 may hold at least a portion of elongated body 110 of cannulating device 100. For example, holder 440 includes a channel 442 for receiving cannulating device 100. Channel 442 may be an extended portion of adapter lumen 420.

In some embodiments, the inner diameters of channel 442 and/or adapter lumen 420 are configured to match the outer diameter of at least a portion of elongated body 110 of cannulating device 100. For example, channel 442 and/or adapter lumen 420 may have a cylindrical, a conical, or a tapered shape with an inner diameter at a location along its length that is substantially the same as the outer diameter of elongated body 110. This allows a portion of cannulating device 100 to be frictionally held steady (e.g., by preventing cannulating device 100 from wiggling) as cannulating device 100 passes through adapter lumen 420 to merge with guidewire 200 (not shown).

As described herein, holder 440 may use any suitable form that allows the introduction of cannulating device 100 over guidewire 200 in a substantially steady fashion. Holder 440 may be formed as a removable part or an integral part of adapter 400. For example, as shown in FIGS. 12A and 12C, holder 440 may have a clamping structure with two deflectable halves that frictionally holds a portion of cannulating device 100. The clamping structure may adaptively deflect inward or outward to receive and frictionally clamp onto portions of cannulating device 100 having different outer diameters. The clamping structure of holder 440 reduces or prevents wiggling of cannulating device 100 as it passes through adapter lumen 420.

FIGS. 13A-13E illustrates another exemplary embodiment of holder 440 of adapter 400.

Figure 13E:
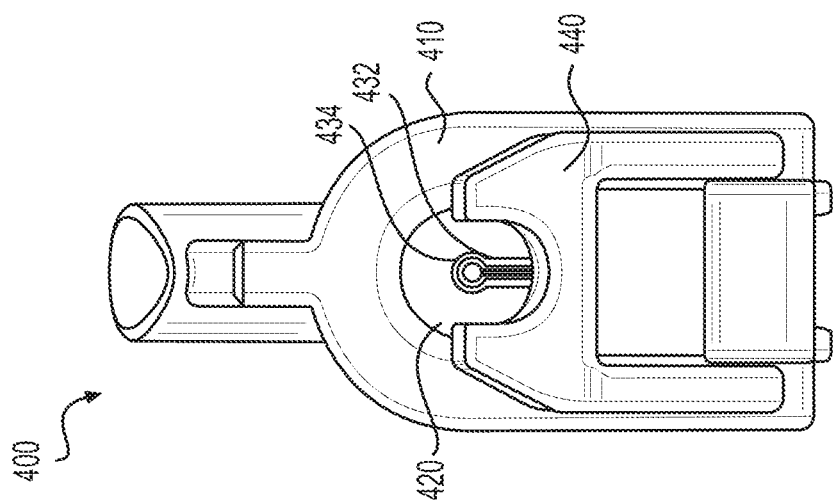
FIG. 13E is a top plan view of the exemplary adapter of FIG. 13A in the second position, according to embodiments of the present disclosure.
Figure 13D:
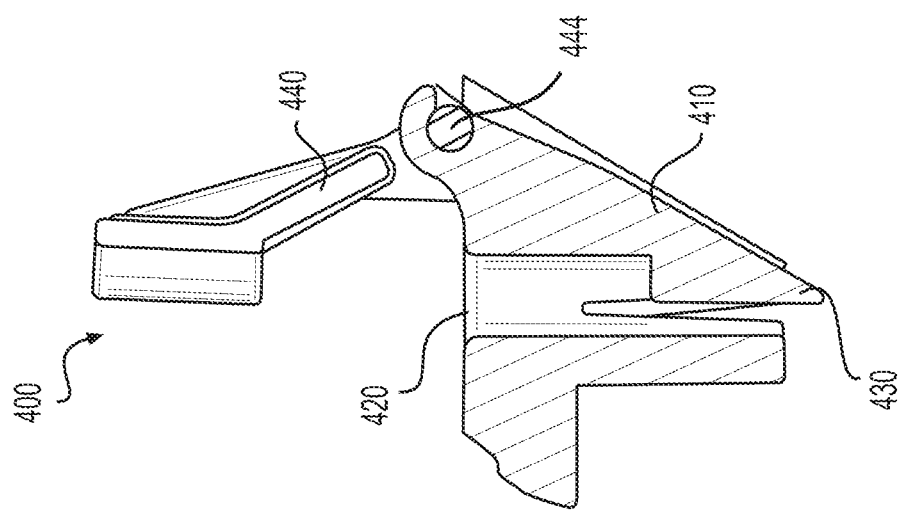
FIG. 13D is a cross-sectional view of the exemplary adapter of FIG. 13A in the second position, according to embodiments of the present disclosure.
Figure 13C:
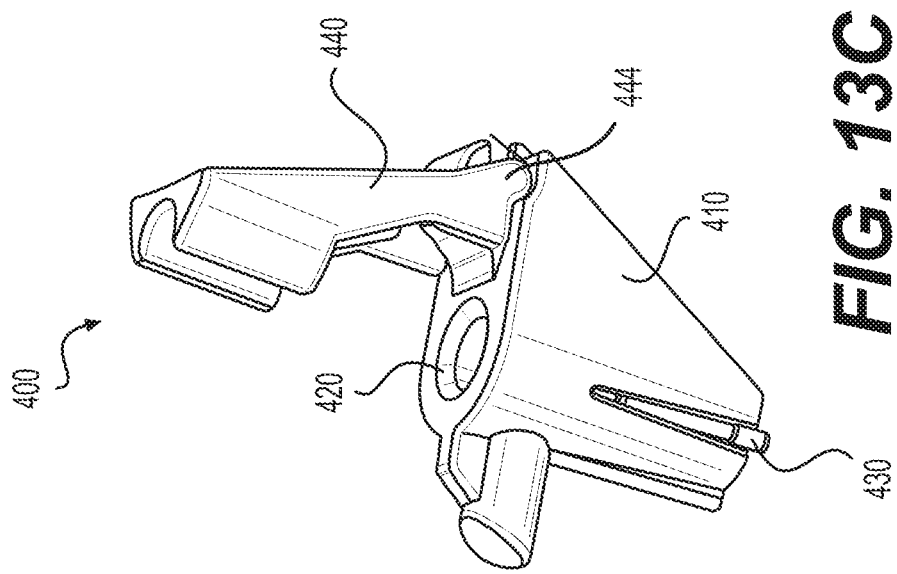
FIG. 13C is a perspective view of the exemplary adapter of FIG. 13A in a second position, according to embodiments of the present disclosure.

FIGS. 13A and 13C are perspective views of another exemplary adapter 400. FIGS. 13B and 13D are cross-sectional views of the exemplary adapter 400 of FIGS. 13A and 13C. FIG. 13E is a top plan view of the exemplary adapter 400 of FIGS. 13C and 13D. As shown in FIGS. 13A-13E, holder 440 is a clamping structure hinged by the opening of adapter lumen 420 and operating in two positions. For example, holder 440 is connected to body 410 of adapter 400 via a hinge 444. In a first position, as shown in FIGS. 13A and 13B, holder 440 of adapter 400 is configured to be detached from cannulating device 100 (now shown). In a second position, as shown in FIGS. 13C-13E, holder 440 aligns with the longitudinal axis of adapter lumen 420 so as to frictionally hold a portion of cannulating device 100 (not shown). The hinged connection between holder 440 and body 410 of adapter 400 allows a physician or medical practitioner to switch the position of holder 440 as needed to effectively merge cannulating device 100 with guidewire 200

FIGS. 14A-15D illustrate various exemplary embodiments of cannulating device 100 with its distal end 130 received by or passing through adapter 400.

FIG. 14A is a perspective view of a distal portion of the exemplary cannulating device 100 of FIG. 6 (an endoscopic catheter) passing by the exemplary adapter 400 of FIGS. 12A-12C. FIG. 14B is a perspective view of a distal portion of the exemplary cannulating device 100 of FIG. 9 passing by the exemplary adapter 400. As shown in FIGS. 14A and 14B, holder 440 may adaptively clamp onto distal ends 130 of cannulating devices 100 having different outer diameters. FIG. 14C is a perspective view of a distal portion of the exemplary cannulating device 100 of FIG. 9 passing by the exemplary adapter 400 of FIGS. 13A-13E. As shown in FIG. 14C, when holder 440 is in the second position, holder 440 frictionally holds at least a portion of distal end 130 of cannulating device 100 to allow cannulating device 100 to pass through adapter 400 in a steady fashion.

FIG. 15A is a perspective view of a distal portion of the exemplary cannulating device 100 of FIG. 10 (an endoscopic sphincterotome) with its distal end 130 passed through the exemplary adapter 400 of FIGS. 12A-12C. FIG. 15B is a perspective view of a distal portion of the exemplary cannulating device 100 of FIG. 10 with its distal end 130 passing by the exemplary adapter 400 of FIGS. 12A-12C. FIG. 15C is a partial perspective view of a distal portion of the exemplary cannulating device of FIG. 10 with its distal end 130 passed through the exemplary adapter 400 of FIGS. 13A-13E. FIG. 15D is a perspective view of the exemplary cannulating device 100 of FIG. 10 with its distal end 130 passing by the exemplary adapter 400 of FIGS. 13A-13E.

As shown in FIGS. 15A and 15C, when cannulating device 100 is an endoscopic sphincterotome, before use, cannulating device 100 may be provided with adapter 400 loaded above distal end 130 or a suitable location along elongated body 110 of cannulating device 100. Alternatively, as shown FIGS. 15B and 15D, cannulating device 100 may be provided with adapter 400 loaded at distal end 130. In such instances, the bendable portion of the endoscopic sphincterotome can become straight when passing through adapter 400 and return to a bent form after passing by adapter 400. Additionally, as illustrated in FIGS. 15A-15D, when distal end 130 of cannulating device 100 has a smaller outer diameter than the remaining portion of cannulating device 100, holder 440 can adaptively adjust its inner diameter to frictionally hold different portions of cannulating device 100 with different outer diameters, including distal end 130.

Figure 16A:
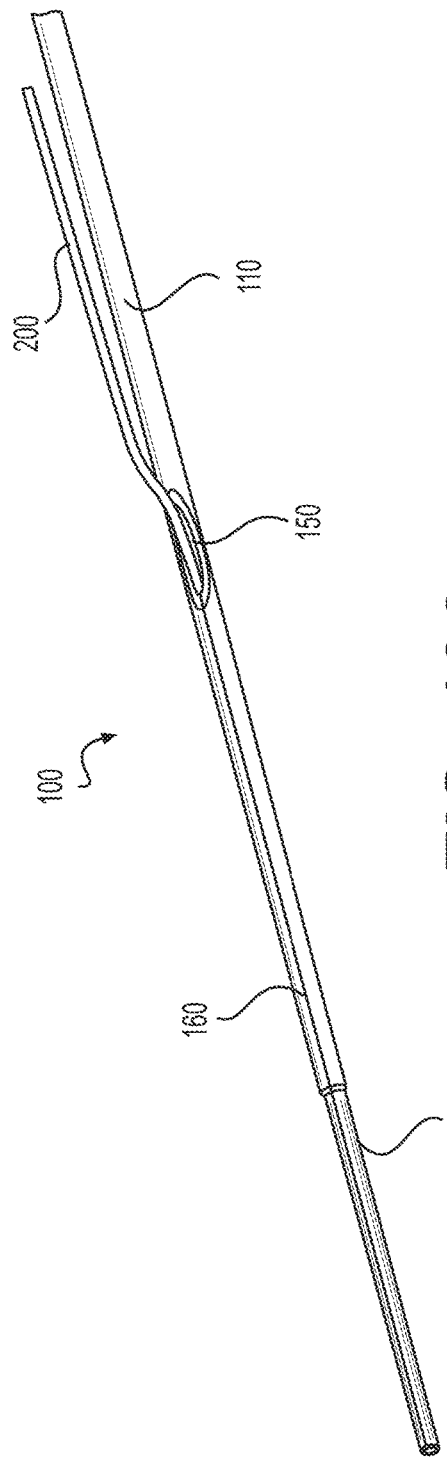
FIG. 16A is a perspective view of a distal portion of an exemplary cannulating device having an opening, according to embodiments of the present disclosure.
Figure 16B:
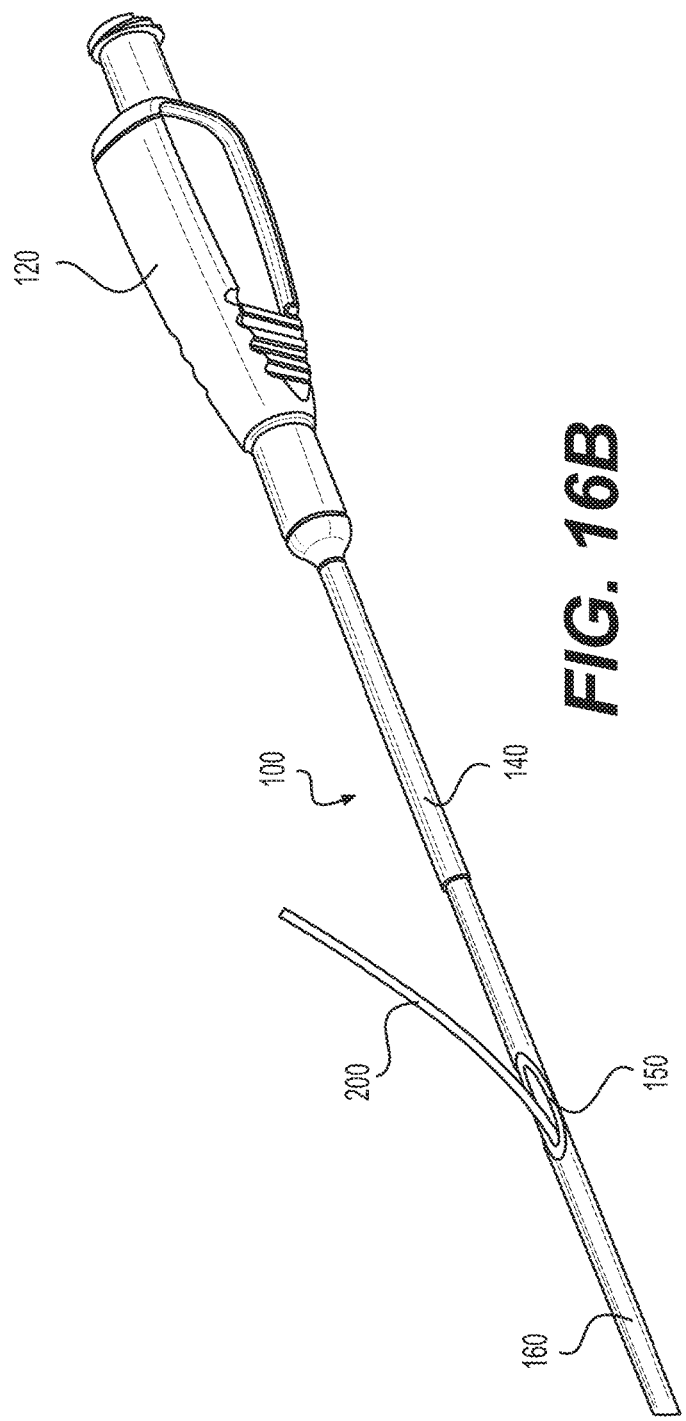
FIG. 16B is a perspective view of a proximal portion of an exemplary cannulating device having an opening, according to embodiments of the present disclosure.

FIG. 16A is a perspective view of a distal portion of an exemplary cannulating device 100 having an opening 150. FIG. 16B is a perspective view of a proximal portion of another exemplary cannulating device 100 having an opening 150. Opening 150 may be formed using any suitable method, such as by skiving or paring a portion of elongated body 110. Opening 150 may extend through the wall of elongated body 110 to reach guidewire lumen 170 inside elongated body 110. Thus, guidewire 200 merged into guidewire lumen 170 may exit through opening 150. Opening 150 may be positioned at any desired portion of elongated body 110 between.

In some embodiments, as shown in FIG. 16A, opening 150 may be located in a distal portion of cannulating device 100, closer to distal end 130 than to proximal end 140 or handle 120. Slit 160 may extend longitudinally from the distal tip of cannulating device 100 up to opening 150. Thus, the remaining portion of cannulating device 100 does not have slit 160. Guidewire 200 merged into guidewire lumen 170 of cannulating device 100 may exit guidewire lumen 170 at opening 150 and further extend parallel to elongated body 110 until it reaches proximal end 140 of cannulating device 100. In such instances, guidewire lumen 170 may also extend longitudinally along elongated body 110 from the distal tip of cannulating device 100 up to opening 150.

In other embodiments, as shown in FIG. 16B, opening 150 may be located in a proximal portion of cannulating device 100, closer to proximal end 140 or handle 120 than to distal end 130. In such instances, slit 160 and guidewire lumen 170 may extend from the distal tip over a substantial length of elongated body 110 up to opening 150. Guidewire 200 merged into guidewire lumen 170 of cannulating device 100 may exit guidewire lumen 170 at opening 150.

Figure 17A:
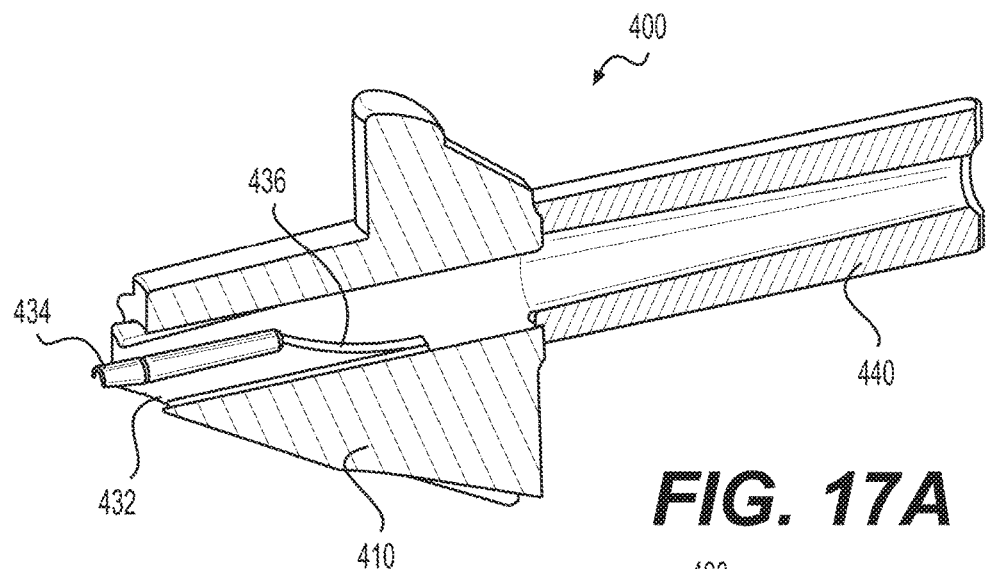
FIG. 17A is a cross-sectional view of another exemplary adapter, according to embodiments of the present disclosure.
Figure 17B:
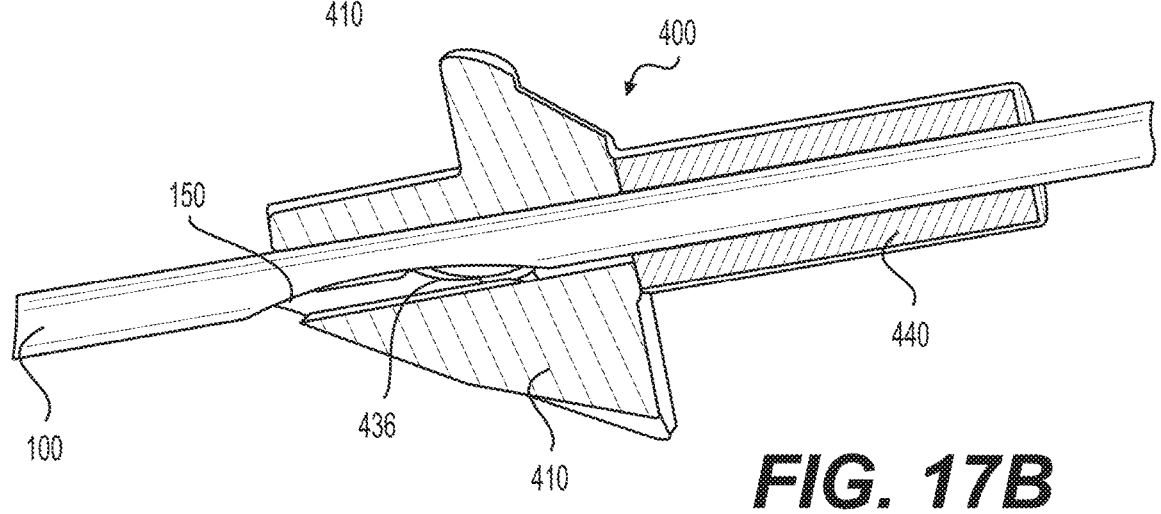
FIG. 17B is a cross-sectional view of an exemplary cannulating device of FIG. 16A or FIG. 16B passing through the exemplary adapter of FIG. 17A, according to embodiments of the present disclosure.
Figure 17C:
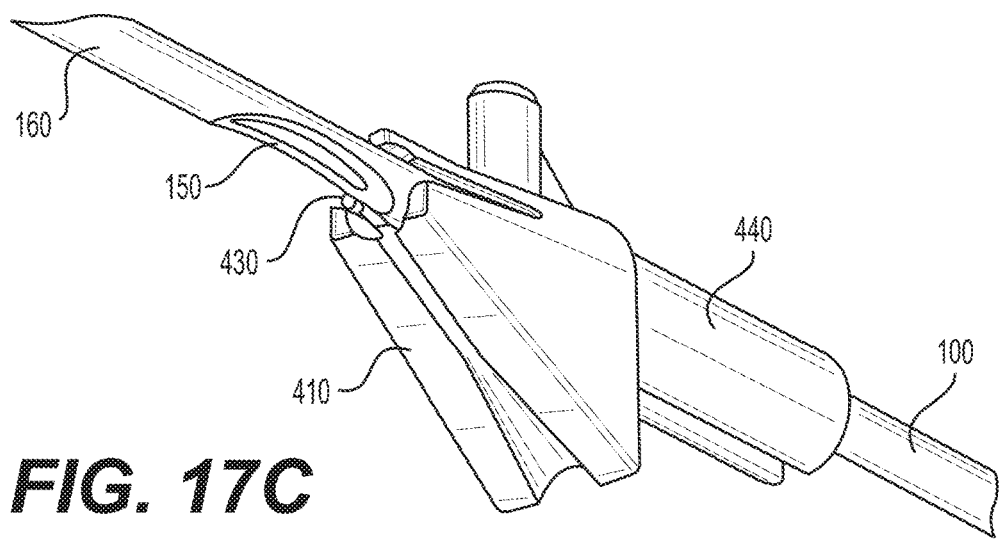
FIG. 17C is a perspective view of the exemplary cannulating device of FIG. 16A or FIG. 16B passing through the exemplary adapter of FIG. 17A, according to embodiments of the present disclosure.

FIGS. 17A-17C illustrate another exemplary adapter 400 for introducing the exemplary cannulating device 100 of FIG. 16A or FIG. 16B having opening 150 over a guidewire 200 (not shown). FIG. 17A is a cross-sectional view of the exemplary adapter 400. FIG. 17B is a cross-sectional view of the exemplary cannulating device 100 of FIG. 16A or FIG. 16B passing through the exemplary adapter 400 of FIG. 17A. FIG. 17C is a perspective view of the exemplary cannulating device 100 of FIG. 16A or FIG. 16B passing through the exemplary adapter 400 of FIG. 17A.

As shown in FIG. 17A, wedge 430 of adapter 400 further includes a ramp portion 436. Ramp portion 436 may be positioned at the top end of wedge 430 and may provide a ramped surface between guide portion 434 and the inner wall of adapter lumen 420. As shown in FIG. 17B, as cannulating device 100 passing through adapter 400, when opening 150 of cannulating device 100 reaches ramp portion 436, cannulating device 100 may move along ramp portion 436 so that wedge 430 slides out of cannulating device 100. Thus, ramp portion 436 allows wedge 430 to dislodge from the non-slitted portion of cannulating device 100 (e.g., from opening 150 to handle 120).

As described herein, other suitable mechanisms may be used for dislodging wedge 430 from the non-slitted portion of cannulating device 100. After opening 150, wedge 430 may be deflected sideways (as shown in FIG. 17C) or remains in its original position as cannulating device 100 continue passing through adapter 400.

FIG. 18 is a perspective view of a proximal portion of the exemplary cannulating device 100 of FIG. 16B with an exemplary guidewire port 190. As shown in FIG. 18, when opening 150 is in a proximal portion of cannulating device 100, cannulating device 100 may optionally include guidewire port 190 positioned around opening 150. Guidewire port 190 may be fixedly or removably attached to elongated body 110 of cannulating device 100. As described herein, guidewire port 190 may have any suitable structures to facilitate a physician to introduce a guidewire 200 into or removing guidewire 200 from guidewire lumen 170 of cannulating device 100. For example, during an endoscopic procedure, a first cannulating device 100 loaded with a guidewire 200 may be introduced through port 310 into endoscope 300 to determine a desired treatment site. Guidewire port 190 may provide guidance for the location of opening 150 and the insertion of guidewire 200 into opening 150 and guidewire lumen 170.

FIG. 19A is a perspective view of the exemplary guidewire port 190 of FIG. 18. FIG. 19B is a cross-sectional view of the exemplary guidewire port 190 of FIG. 19A. As shown in FIGS. 19A and 19B, guidewire port 190 may include a port lumen 192 through which cannulating device 100 may pass. Guidewire port 190 may additionally include port inlet 194, through which a guidewire 200 may enter opening 150 and further into guidewire lumen 170 of cannulating device 100.

Guidewire port 190 may also include port slit 196. Port slit 196 may extend between a distal opening of guidewire port 190 and port inlet 194. Port slit 196 may be aligned with slit 160 of cannulating device 100. In some embodiments, the width of slit 196 may be larger than the diameter of a guidewire 200 to be introduced into guidewire lumen 170 of cannulating device 100. Thus, a portion of guidewire 200 may be passed through port slit 196 when guidewire 200 is locked in place. In some embodiments, the width of slit 196 may be larger than the natural width of slit 160.

As shown in FIG. 19B, guidewire port 190 may further include a steering portion 198 extending along the inner surface of port lumen 192. Steering portion 198 steers a guidewire 200 inserted through port inlet 194 towards the distal opening of port lumen 192 to enter opening 150 and/or guidewire lumen 170 of cannulating device 100.

Figure 20:
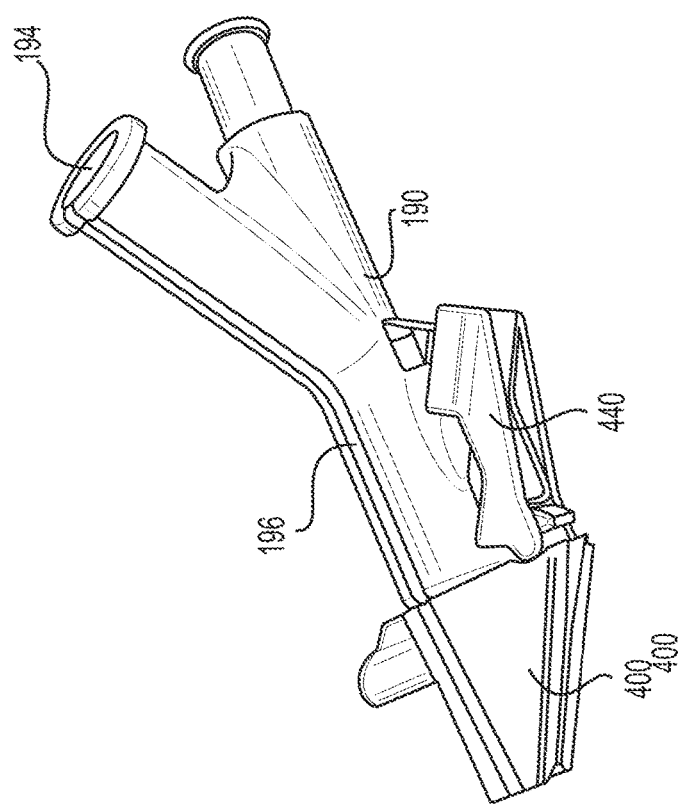
FIG. 20 is a perspective view of the exemplary guidewire port of FIG. 19 attached to the exemplary adapter of FIGS. 13A-13E, according to embodiments of the present disclosure.
Figure 21:
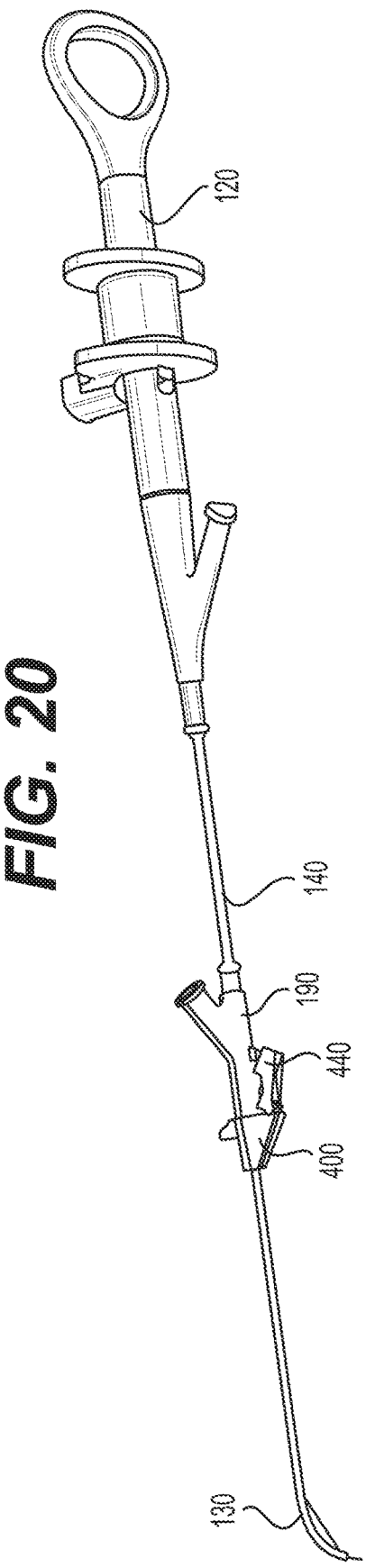
FIG. 21 is a perspective view of another exemplary cannulating device with the exemplary guidewire port of FIG. 19A attached to the exemplary adapter of FIGS. 13A-13E, according to embodiments of the present disclosure.

FIG. 20 is a perspective view of the exemplary guidewire port 190 of FIG. 19 attached to the exemplary adapter 400 of FIGS. 13A-13E. FIG. 21 is a perspective view of an exemplary cannulating device 100 with the exemplary guidewire port of FIG. 19A attached to the exemplary adapter 400 of FIGS. 13A-13E. As shown in FIGS. 20 and 21, guidewire port 190 may be provided together with adapter 400. For example, holder 440 of adapter 400 may clamp onto a portion of guidewire port 190 such that adapter lumen 420 and port lumen 192 are aligned for receiving cannulating device 100 therethrough. Before the introduction of cannulating device 100 over a guidewire 200 fixed in place, adapter 400 may be removed from guidewire port 190 and engaged with endoscopic block 500.

Figure 22:
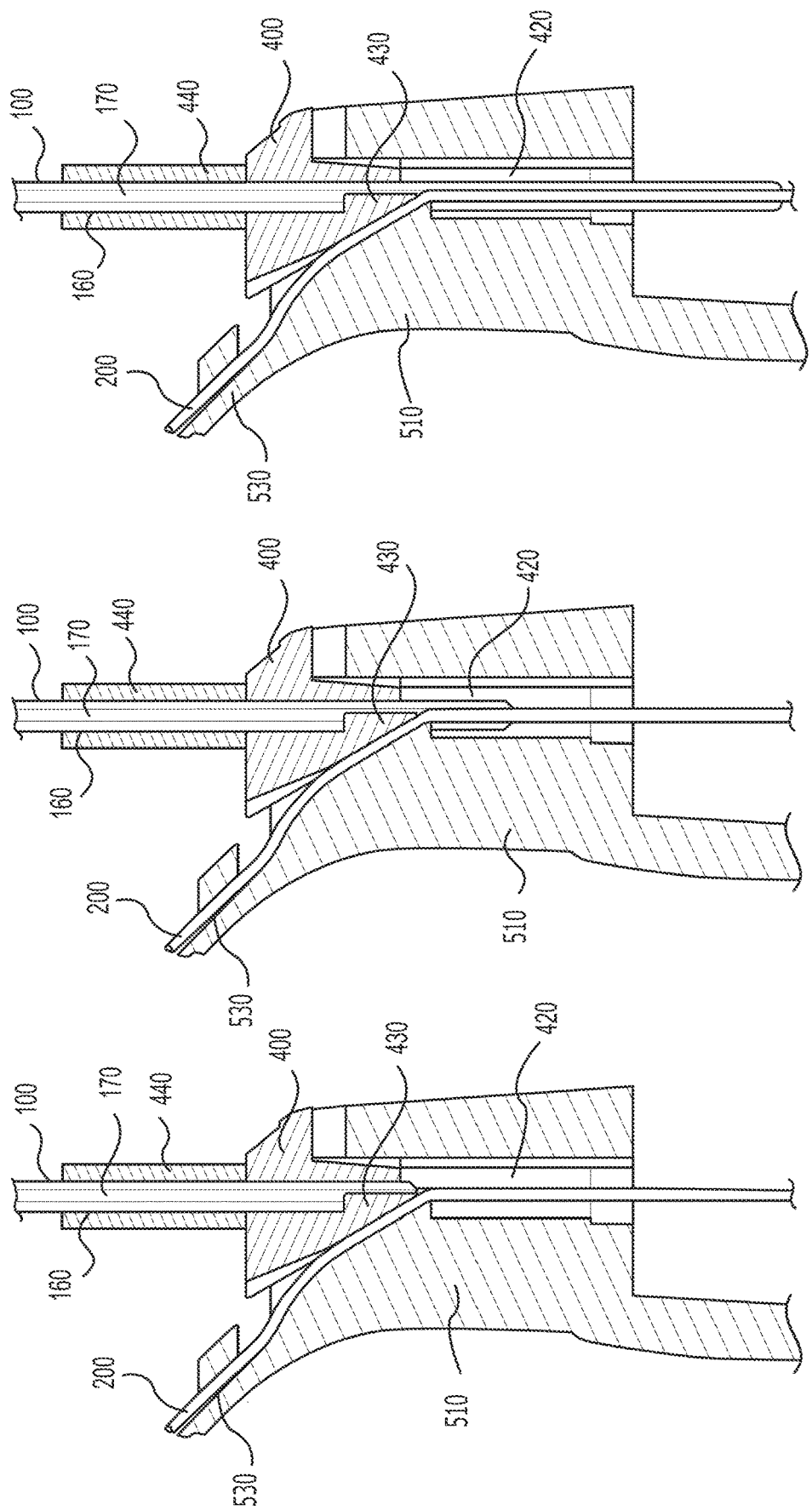
FIG. 22A is a perpendicular cross-sectional view of the exemplary adapter of FIGS. 12A-12C, receiving an exemplary cannulating device, according to embodiments of the present disclosure.
FIG. 22B is a perpendicular cross-sectional view of the exemplary adapter of FIGS. 12A-12C, receiving an exemplary cannulating device, according to embodiments of the present disclosure.
FIG. 22C is a perpendicular cross-sectional view of the exemplary adapter of FIGS. 12A-12C, receiving an exemplary cannulating device, according to embodiments of the present disclosure.

FIGS. 22A-22C are perpendicular cross-sectional views of system 10 for introducing cannulating device 100 over guidewire 200 at different stages. As described above, before introducing cannulating device 100 over guidewire 200, guidewire 200 can be fixed by locking device 530 in a predetermined position to maintain access to a desired treatment site.

As shown in FIG. 22A, to introduce cannulating device 100 over guidewire 200, a physician or an assistant may insert cannulating device 100 into adapter lumen 420 of adapter 400. In some embodiments, to facilitate the alignment of cannulating device 100 with wedge 430 and/or guidewire 200, the inner diameter of adapter lumen 420 may be selected to substantially match an outer diameter of cannulating device 100. As cannulating device 100 passes through adapter lumen 420, the distal tip of cannulating device 100 meets and passes by wedge 430, which then wedges open a portion of slit 160 of cannulating device 100.

As shown in FIG. 22B, the opening of slit 160 by wedge 430 allows a portion of guidewire 200 at a distal end of wedge 430 to merge into a corresponding portion of cannulating device 100, e.g., a portion of guidewire lumen 170, through the opened portion of slit 160. After guidewire 200 merges into the distal tip of cannulating device 100, as shown in FIG. 22C, guidewire 200 can continuously merge into cannulating device 100 as cannulating device 100 passes though adapter lumen 420 until the distal end of cannulating device 100 approximates or reaches the desired treatment site.

As described above, guidewire 200 is held in place by locking device 530 throughout the merging of guidewire 200 into cannulating device 100. This advantageously reduces the risk of losing the access to the desired treatment site in the body of a patient and increases the effectiveness of the introduction of cannulating device 100 over guidewire 200 in a minimum amount of time.

As described herein, cannulating device 100 with slit 160 may be made of any suitable compliant polymeric material with adequate stiffness such that it can be wedged open and can close on its own. Such polymeric material may be selected from PTFE, Pebax, Nylon, Polyethylene, etc.

To retrieve cannulating device 100 introduced over guidewire 200, a physician or an assistant may remove adapter 400 from endoscopic block 500 and pull cannulating device 100 out of the inner lumen of endoscope 300 and endoscopic block 500. Guidewire 200 can remain locked by locking device 530 of endoscopic block 500 so that a subsequent cannulating device 100 may be introduced to the treatment site. During the retrieval of cannulating device 100, to remove cannulating device 100 off guidewire 200, the physician or assistant may separate cannulating device 100 from guidewire 200 by continuously splitting or tearing cannulating device 100 from guidewire 200 through slit 160 without performing the long wire or short wire exchange.

System 10, cannulating device 100, and/or adapter 400 described herein may be utilized in a variety of systems and methods for introducing endoscopic devices or performing device exchange during endoscopic procedures. An exemplary method 600 may use one or more features of the embodiments system 10, such as cannulating device 100 and adapter 400, described above in reference to FIGS. 1-22C. Exemplary embodiments of method 600 are described below with reference to FIG. 23.

As described herein, some or all steps of method 600 may be performed by system 10 or one or more components of system 10. The sequence of the steps of method 600 may change, and may be performed in various exemplary embodiments. Additional steps may be added to method 600. Some steps may be omitted or repeated, and/or may be performed simultaneously.

Figure 23:
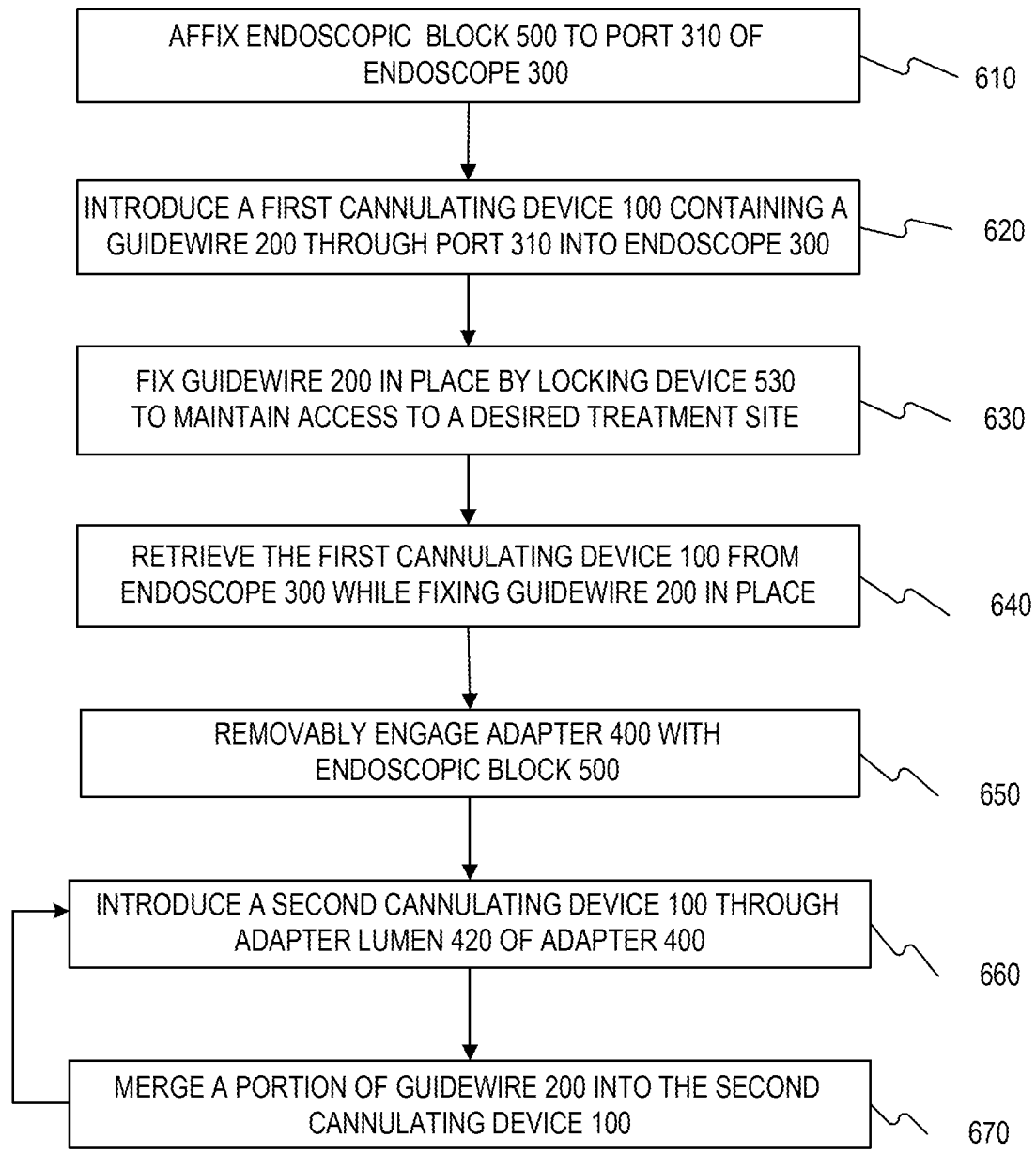
FIG. 23 is a flowchart of an exemplary method for introducing or exchanging endoscopic devices, according to embodiments of the present disclosure.

As described above, in some embodiments, adapter 400 can be removably engaged with endoscopic block 500. In such instances, method 600 may include steps 610-670 as shown in FIG. 23. Step 610 may include affixing endoscopic block 500 of system 10 to port 310 of endoscope 300. For example, fastener 520 as shown in FIG. 1 may be used to securely attach endoscopic block 500 on top of port 310 such that endoscopic block 500 aligns with the inner lumen of port 310.

Step 620 may include introducing a first cannulating device 100 loaded with a guidewire 200 through port 310 into endoscope 300 to approximate a desired treatment site. Step 620 may further include performing a diagnostic operation to determine the desired treatment site.

Step 630 may include fixing guidewire 200 in place to maintain access to the desired treatment site. For example, step 630 may include frictionally fixing guidewire 200 in place by a plurality of zigzag locking features of locking device 530 of endoscopic block 500.

Step 640 may include retrieving the first cannulating device 100 from endoscope 300 while fixing guidewire 200 in place by locking device 530. Step 640 may further include continuously retracting and splitting the first cannulating device 100 from a proximal end or distal end of guidewire 200 through slit 160 until the first cannulating device 100 is completely removed off guidewire 200. In some embodiments, when cannulating device 100 includes opening 150 at its distal portion, step 640 may first include continuously retracting the first cannulating device 100 up to opening 150, and then retracting and splitting the first cannulating device 100 from guidewire 200 through slit 160 until the first cannulating device 100 is removed from the inner lumen of endoscope 300.

Step 650 may include removably engaging adapter 400 with endoscopic block 500. Step 650 may further include removably engaging adapter 400 with an opening of endoscopic block 500. For example, adapter 400 may engage with endoscopic block 500 via frictional fit, threaded fit, or other suitable fitting mechanism. Additionally or alternatively, step 650 may include engaging adapter 400 with endoscopic block 500 using a detent, a fastener, and/or other suitable structures to securely hold adapter 400 thereon.

Step 660 may include introducing a second cannulating device 100 through adapter lumen 420 of adapter 400. Step 660 may also include passing the distal tip of the second cannulating device 100 by wedge 430 of adapter 400 and wedging open a portion of slit 160 of the second cannulating device 100 by wedge 430. Step 660 may further include holding at least a portion of the second cannulating device 100 by holder 440 of adapter 400 such that the second cannulating device 100 may pass through adapter lumen 420 and merge with guidewire 200 in a steady fashion.

Step 670 may include merging a portion of guidewire 200 into the second cannulating device 100 through the opened portion of slit 160. Step 670 may further include, after merging the portion of guidewire 200 into the second cannulating device 100, receiving the portion of guidewire 200 in guidewire lumen 170 of the second cannulating device 100. Step 670 may further include closing or narrowing the opened portion of slit 160 to retain the portion of guidewire 200 in guidewire lumen 170 after the corresponding portion of the second cannulating device 100 passes by wedge 430. Steps 660 and 670 may be performed continuously until the distal end of the second cannulating device 100 reaches the desired treatment site.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An apparatus for endoscopic procedures, the apparatus comprising:
   a cannulating device, comprising:
      an elongated body comprising a guidewire lumen configured to receive a guidewire therein; and
      a slit extending over at least a portion of the length of the elongated body from a distal tip to a proximal position of the elongated body; and
   an adapter configured to merge the guidewire into the guidewire lumen, the adapter comprising:
      an adapter lumen configured to receive the elongated body;
      a groove extending along an outer surface of the adapter, the groove configured to receive the guidewire and to lead the guidewire towards the adapter lumen; and
      a wedge extending from an inner surface of the adapter lumen, the wedge configured to widen a portion of the slit such that a portion of the guidewire merges into the guidewire lumen through the widened portion of the slit.

2. The apparatus of claim 1, wherein the widened portion of the slit returns to a natural width after passing by the wedge such that the portion of the guidewire is retained within the guidewire lumen.

3. The apparatus of claim 1, wherein the adapter lumen has an inner diameter that substantially matches the outer diameter of at least a portion of the elongated body.

4. The apparatus of claim 1, wherein the adapter further comprises a holder configured to hold at least a portion of the elongated body.

5. The apparatus of claim 4, wherein the holder comprises a channel for receiving the elongated body, an inner diameter of the channel configured to match the outer diameter of at least a portion of the elongated body.

6. The apparatus of claim 5, wherein the channel has a tapered shape configured to frictionally hold at least a portion of the elongated body.

7. The apparatus of claim 5, wherein the holder comprises two deflectable halves configured to frictionally hold at least a portion of the elongated body.

8. The apparatus of claim 4, wherein the holder comprises a clamp hinged by an opening of the adapter lumen and configured to operate in two positions, wherein in a first position, the holder is removed from the cannulating device, and in a second position, the holder frictionally holds the cannulating device.

9. The apparatus of claim 1, wherein the adapter is fixedly or removably engaged with an endoscopic block, wherein the guidewire is retained by the endoscopic block.

10. The apparatus of claim 1, wherein the cannulating device further comprises an opening where the guidewire enters or exits from the guidewire lumen.

11. The apparatus of claim 10, wherein the wedge further comprises a ramp such that the wedge slides out of the cannulating device when the opening of the cannulating device passes by the wedge.

12. A method for cannulation, the method comprising:
   providing a cannulating device having:
      an elongated body comprising a guidewire lumen configured to receive a guidewire therein; and
      a slit extending over at least a portion of the length of the elongated body from a distal tip to a proximal position of the elongated body; and
   providing an adapter configured to merge the guidewire into the guidewire lumen, the adapter comprising:
      an adapter lumen configured to receive the elongated body;
      a groove extending along an outer surface of the adapter, the groove configured to receive the guidewire and to lead the guidewire towards the adapter lumen; and
      a wedge extending from an inner surface of the adapter lumen;
   receiving the elongated body within the adapter lumen such that the wedge engages and widens a portion of the slit; and
   merging the portion of a guidewire into the guidewire lumen through the widened portion of the slit.

13. The method of claim 12, further comprising merging the guidewire into the guidewire lumen until a portion of the guidewire exits an opening of the cannulating device.

14. The method of claim 12, further comprising receiving the elongated body through the adapter lumen until a distal end of the cannulating device reaches a desired treatment site.

15. The method of claim 12, further comprising, before merging the portion of the guidewire into the guidewire lumen, engaging the adapter with an opening of an endoscopic block, wherein the guidewire is retained by the endoscopic block.

* * * * *